United States Patent
Kim et al.

(10) Patent No.: US 10,655,839 B2
(45) Date of Patent: May 19, 2020

(54) LIGHT SOURCE UNIT

(71) Applicant: LG INNOTEK CO., LTD., Seoul (KR)

(72) Inventors: Cheon Joo Kim, Seoul (KR); Do Hwan Kim, Seoul (KR); Tae Young Choi, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 0 days.

(21) Appl. No.: 16/481,909

(22) PCT Filed: Feb. 9, 2018

(86) PCT No.: PCT/KR2018/001775
§ 371 (c)(1),
(2) Date: Jul. 30, 2019

(87) PCT Pub. No.: WO2018/147688
PCT Pub. Date: Aug. 16, 2018

(65) Prior Publication Data
US 2020/0041115 A1     Feb. 6, 2020

(30) Foreign Application Priority Data

Feb. 10, 2017 (KR) .......... 10-2017-0018611
Apr. 11, 2017 (KR) .......... 10-2017-0046727

(51) Int. Cl.
*F21V 31/00* (2006.01)
*F21V 15/01* (2006.01)
(Continued)

(52) U.S. Cl.
CPC .............. *F21V 31/005* (2013.01); *F21V 9/32* (2018.02); *F21V 15/01* (2013.01); *F21V 19/003* (2013.01); *F21Y 2115/10* (2016.08)

(58) Field of Classification Search
CPC ........ F21V 31/005; F21V 19/003; F21V 9/32; F21V 15/01
See application file for complete search history.

(56) References Cited

U.S. PATENT DOCUMENTS 8,405,096 B2 *   3/2013   Chen .................. H01L 33/60
                                                      257/79
2009/0196034 A1   8/2009  Gherardini et al.
(Continued)

FOREIGN PATENT DOCUMENTS

JP      3182496       3/2013
KR      10-0910634    8/2009
(Continued)

OTHER PUBLICATIONS

International Search Report dated May 16, 2018 issued in Application No. PCT/KR2018/001775.

*Primary Examiner* — Evan P Dzierzynski
(74) *Attorney, Agent, or Firm* — Ked & Associates, LLP

(57) ABSTRACT

A light source unit disclosed in an embodiment of the invention includes: a first cover having an open region at an upper portion and a recess in which a lower portion is opened; a second cover coupled to the lower portion of the first cover; a light source module disposed between the first and second covers and having a circuit board and a light emitting device on the circuit board; a waterproof film disposed on the light emitting device and facing an upper surface of the circuit board; and first and second gaskets on the upper surface of the circuit board. The first cover and the second cover are coupled to each other by protrusions and grooves and are bonded to each other by a bonding portion.

20 Claims, 17 Drawing Sheets

(51) Int. Cl.
  *F21V 9/32* (2018.01)
  *F21V 19/00* (2006.01)
  *F21Y 115/10* (2016.01)

(56) References Cited

U.S. PATENT DOCUMENTS

| | | | |
|---|---|---|---|
| 2010/0135020 A1* | 6/2010 | Moore | A47F 11/10 362/249.02 |
| 2010/0296265 A1 | 11/2010 | Kim et al. | |
| 2012/0074434 A1* | 3/2012 | Park | H01L 33/486 257/88 |
| 2018/0010784 A1 | 1/2018 | Kim et al. | |

FOREIGN PATENT DOCUMENTS

| | | |
|---|---|---|
| KR | 10-2010-0095654 | 8/2010 |
| KR | 10-2010-0131209 | 12/2010 |
| KR | 20-2011-0002372 | 3/2011 |
| KR | 10-2015-0050205 | 5/2015 |
| KR | 10-1621804 | 5/2016 |
| KR | 10-2016-0092685 | 8/2016 |
| KR | 10-2017-0022073 | 3/2017 |

\* cited by examiner

300

LIGHT SOURCE UNIT

CROSS-REFERENCE TO RELATED PATENT APPLICATIONS

This application is a U.S. National Stage Application under 35 U.S.C. § 371 of PCT Application No. PCT/KR2018/001775, filed Feb. 9, 2018, which claims priority to Korean Patent Application Nos. 10-2017-0018611, filed Feb. 10, 2017 and 10-2017-0046727 filed Apr. 11, 2017, whose entire disclosures are hereby incorporated by reference.

TECHNICAL FIELD

An embodiment relates to a light source unit.
An embodiment provides a light source unit having a waterproof and moisture-proof member.

BACKGROUND ART

Light emitting diodes (LEDs) may be formed using a compound semiconductor material such as GaAs-based, AlGaAs-based, GaN-based, InGaN-based and InGaAlP-based materials.

Such a light-emitting diode is used as a light-emitting device that is packaged and emits various colors and the light-emitting device is used as a light source in various applications such as a light indicator to indicate color, a character indicator, and an image indicator.

In particular, ultraviolet light emitting diodes (UV LEDs) may be used for sterilization, purification or the like in a case of a short wavelength, and may be used in a light-emitting apparatus or a curing apparatus in a case of a long wavelength. However, since an environment in which the ultraviolet ray emitting diode using the short wavelength is applied is often high humidity or underwater, the apparatus may be defective due to deterioration of a moisture-proof and waterproof function thereof and the operation reliability may be decreased.

DISCLOSURE

Technical Problem

An embodiment of the invention provides a light source unit having a new waterproof and moisture-proof structure.

An embodiment of the invention provides a light source unit having a double gasket structure around an outer periphery of a light emitting device.

An embodiment of the invention provides a light source unit in which an outer side of a waterproof film covering a light emitting device is disposed between double gaskets.

An embodiment of the invention provides a light source unit having a waterproof member bonded along the outer peripheries of first and second covers.

An embodiment of the invention provides a light source unit in which a waterproof member for bonding the first and second covers to each other is positioned inside an outer wall of the first and second covers.

An embodiment of the invention provides a light source unit capable of protecting the light source module inside the first and second covers by molding the first and second covers with a molding member.

An embodiment of the invention may improve the reliability of a light source unit having an ultraviolet light source.

Technical Solution

A light source unit according to an embodiment of the invention comprises: a first cover including an open region at an upper portion thereof and a recess in which a lower portion is opened; a second cover coupled to the lower portion of the first cover; a light source module disposed between the first and second covers, the light source module having a circuit board and a light emitting device on the circuit board; a waterproof film disposed on the light emitting device and facing an upper surface of the circuit board; a first gasket including a first opening therein and disposed between the waterproof film and the circuit board; a second gasket including a second opening therein and disposed on the waterproof film, wherein the first cover includes a first outer wall to an outer periphery and the second cover includes a second outer wall to an outer periphery, wherein one of the first outer wall and the second outer wall has a protrusion and the other has a groove, wherein the protrusion is coupled to the groove, and a bonding portion is disposed between the first outer wall and the second outer wall, wherein the light emitting device is disposed in a first opening of the first gasket, and an upper surface of the light emitting device may faces to the second opening of the second gasket and the open region of the first cover.

A light source unit according to an embodiment of the invention comprises: a first cover including an open region at an upper portion thereof and a recess in which a lower portion is opened; a second cover coupled to the lower portion of the first cover and having a receiving region at an upper portion thereof, a light source module disposed on the recess of the first cover, the light source module having a circuit board and a light emitting device on the circuit board; a waterproof film disposed on the light emitting device and facing an upper surface of the circuit board; a first waterproof member having a plurality of gaskets outside the light emitting device; a second waterproof member having a bonding portion that outer walls of the first cover and the second cover are bonded to each other; and a molding member disposed in the receiving region of the second cover, wherein the second cover includes a cable hole connected to the receiving region therein and a guide protrusion protruding in an upward direction of the second cover along a periphery of the cable hole, wherein the molding member may be disposed at an inner region and an outer region of the guide protrusion.

According to an embodiment of the invention, the bonding portion is continuously disposed along the first outer wall of the first cover and the second outer wall of the second cover, and the bonding portion includes a plurality of bonding portions disposed a different regions of the first and second outer walls facing each other, and the plurality of bonding portions may have different heights.

According to an embodiment of the invention, the first gasket has a thickness greater than a thickness of the light emitting device, and the first gasket has a plurality of upper protrusions on an upper surface thereof, a first concave region between the plurality of upper protrusions, a plurality of lower protrusions on a lower surface thereof, and a second concave region between the plurality of lower protrusions, wherein the plurality of upper protrusions and the plurality of lower protrusions may be disposed to overlap in a vertical direction.

According to an embodiment of the invention, the first cover includes a first recess in which the first and second gaskets and the waterproof film are disposed, a second recess in which the circuit board is disposed, and a fastening portion for fastening the circuit board to the first cover with a fastening member at an outer side of the first recess.

According to an embodiment of the invention, the first opening has a width larger than a width of the second opening in a first direction, the second opening has the width smaller than the width of the first opening and greater than a width of the light emitting device in the first direction, wherein the width of the second opening in the first direction may be greater than an width of the open region.

According to an embodiment of the invention, the protrusion protrudes from an lower surface of the first outer wall of the first cover toward the second cover, and the groove is recessed on the second outer wall of the second cover, wherein the bonding portion includes a first bonding portion bonded to at least one of surfaces of the protrusion and the groove and a second bonding portion bonded to an inside of the lower surface of the first outer wall and an upper surface of the second outer wall, wherein the first and second bonding portions are formed of at least one of materials of the first and second covers, wherein the first bonding portion is lower than a height of the second bonding portion, the first bonding portion is disposed outside the second bonding portion, and the first and second bonding portions are merged to a materials of the first and second covers.

According to an embodiment of the invention, the light emitting device emits a wavelength band of 100 nm to 280 nm, and the waterproof film, the first and second gaskets may include a fluororesin material.

According to an embodiment of the invention, a guide protrusion protruding from the receiving region of the second cover toward the first cover and a connector coupled to the circuit board are disposed inside the guide protrusion, wherein the first cover is provided with a concave portion having the open region on an upper portion thereof, wherein the concave portion includes an inclined side surface and at least a part of the light emitting device or at least a part of the waterproof film may protrude into the open region.

According to an embodiment of the invention, the circuit board may include a plurality of fastening holes to which the fastening members are fastened, and a metal layer disposed along an outer periphery of the circuit board.

According to an embodiment of the invention, a molding member disposed in the recess of the first cover and the receiving region of the second cover, wherein the second cover includes a cable hole connected to the receiving region and a guide protrusion protruding in an upper direction of the second cover along a periphery of the cable hole, wherein the molding member is disposed in an inner region and an outer region of the guide protrusion, and the second cover may include connection holes disposed at opposite sides of each other around the cable hole on a bottom of the receiving region.

Advantageous Effects

The light source unit according to the embodiment of the invention may be provided with a waterproof unit in a product which is applied to high humidity and water environment.

In the light source unit according to the embodiment of the invention, since the light emitting device is covered with the waterproof film and the waterproof film is closely contacted with the double gaskets, the reliability of the moisture proof unit may be improved.

In the light source unit according to the embodiment of the present invention, the waterproof member for fusing the upper and lower covers for protecting the inner light emitting device may be disposed to block the moisture penetrating in a lateral direction.

In the light source unit according to the embodiment of the invention may protect the connector and the circuit board by molding a periphery of the circuit board and the connector inside thereof with the molding member.

The light source unit according to the embodiment of the invention may be provided as a sterilizing apparatus in a high humidity environment and in water.

BEST MODEL

Figure 1:
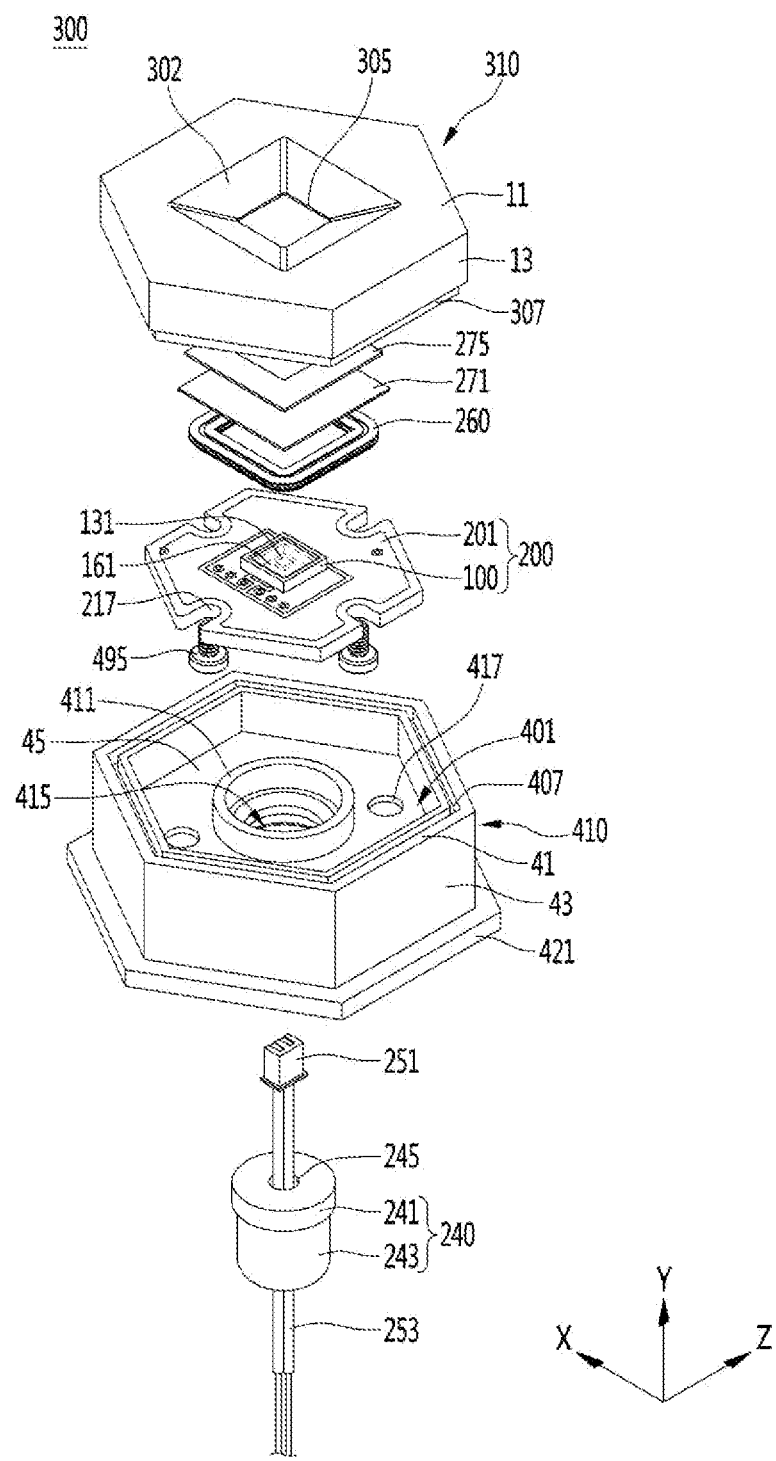
FIG. 1 is an exploded perspective view of a light source unit according to an embodiment of the invention.

Hereinafter, embodiments of the present invention will be described in detail with reference to the attached drawings so as to be easily carried out the present invention by those of ordinary skill in the art to which the invention pertains. However, the present invention may be embodied in many different forms and is not limited to the embodiments described herein.

Throughout the specification, when it is stated a portion "includes" a certain component, this means that it does not exclude other components unless specifically stated otherwise, but may also further include other components. In order to clearly explain the present invention in the drawings, portions which are not related to the description are omitted and similar portions are denoted by similar reference numerals throughout the specification.

In the description of an embodiment, when a portion such as a layer, a film, an region, and a plate is referred to as being "on" another portion, it includes not only a case where it is "directly on" another portion but also a case where there is another portion therebetween. On the contrary, when a portion is "directly on" another portion, it means that there is no other portion therebetween.

A light source unit according to an embodiment of the invention will be described with reference to the attached drawings.

Figure 2:
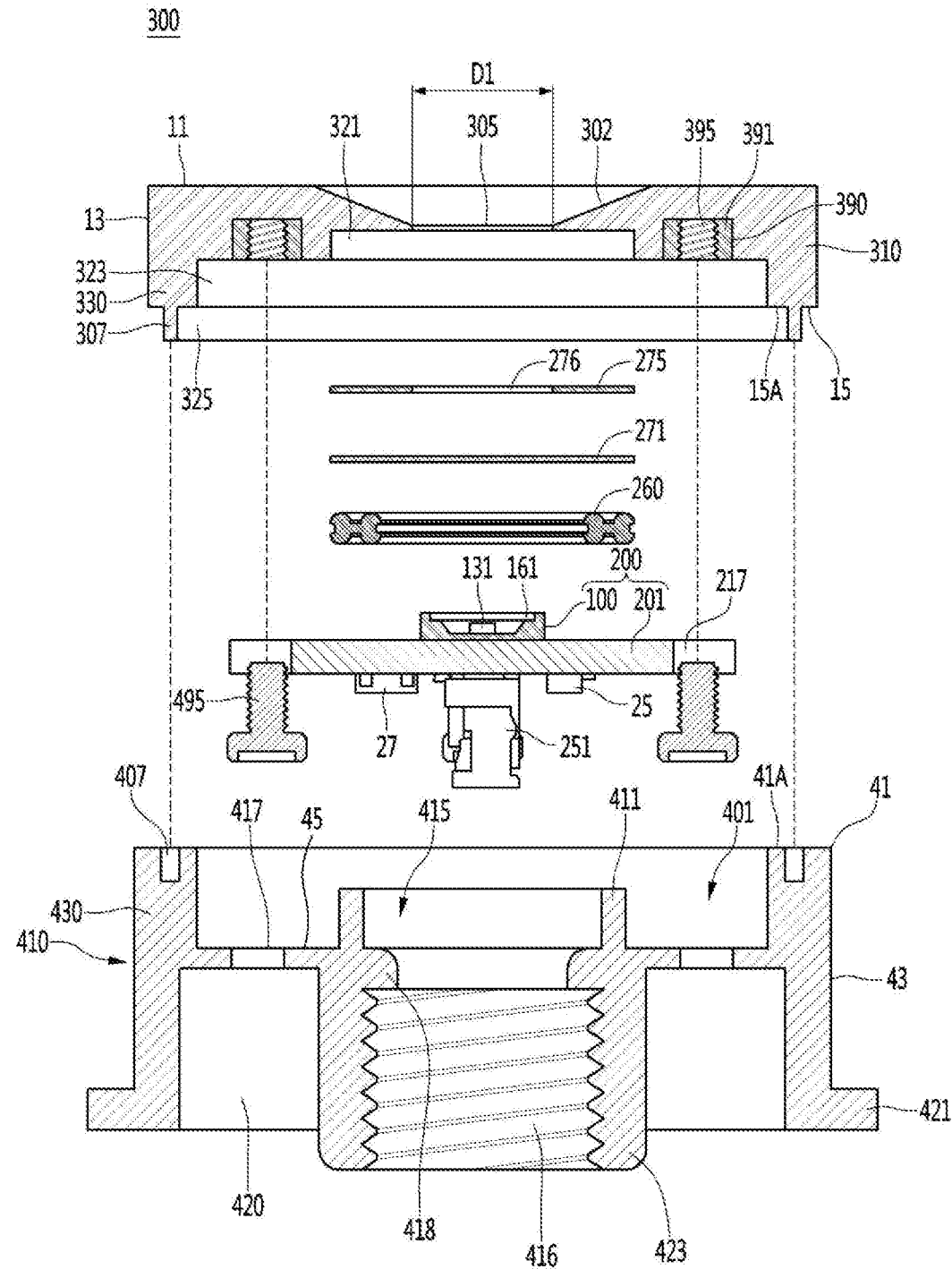
FIG. 2 is a side sectional view showing the exploded state of the light source unit of FIG. 1.
Figure 3:
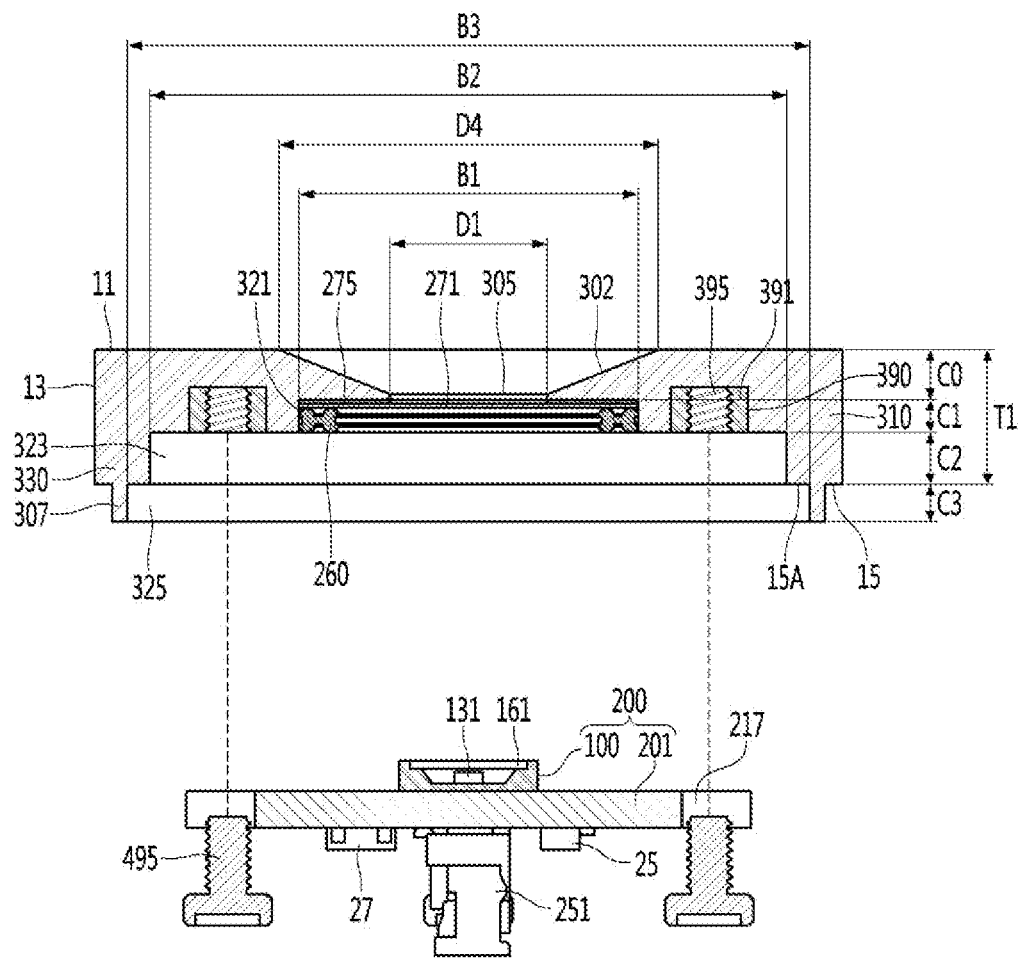
FIG. 3 is a side cross-sectional view illustrating an example of coupling the first cover and the light source module of FIG. 2.
Figure 4:
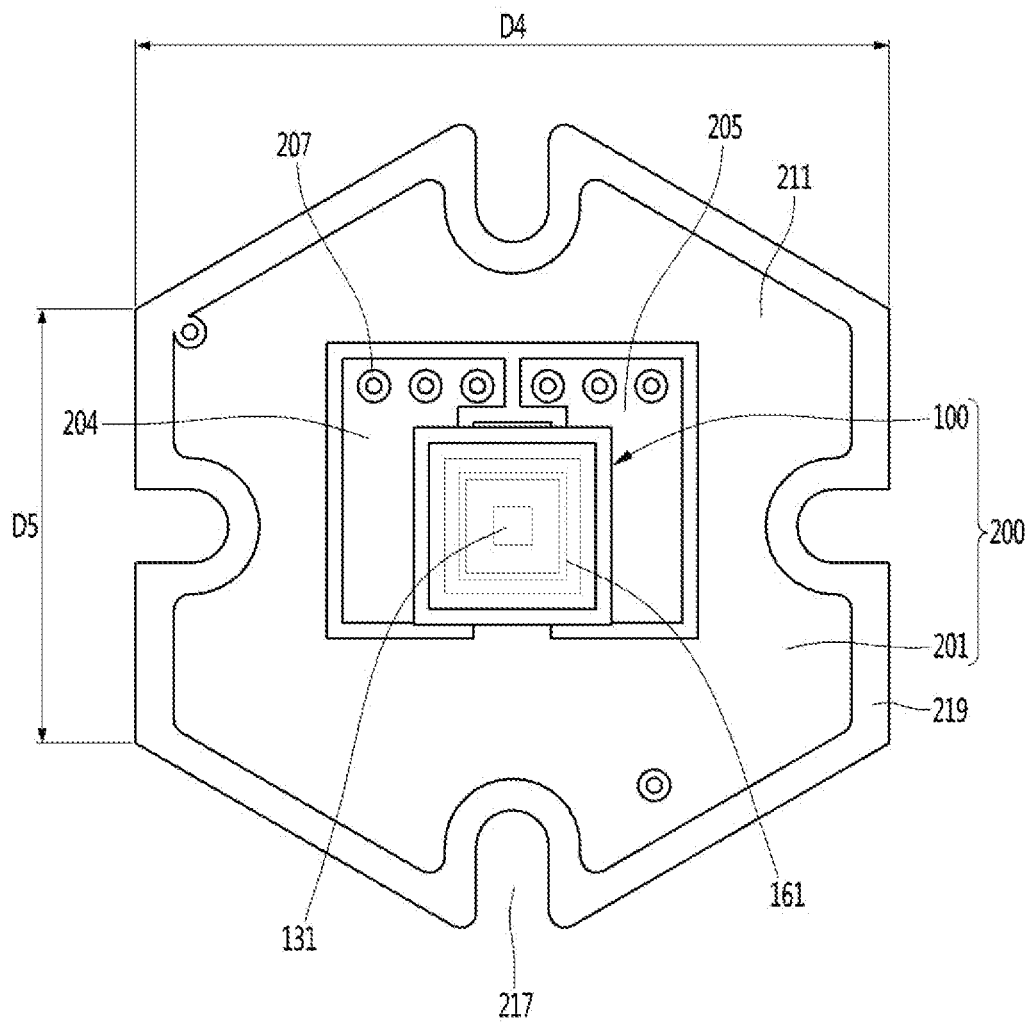
FIG. 4 is a front view showing an example of a circuit board of the light source module of FIG. 1.
Figure 5:
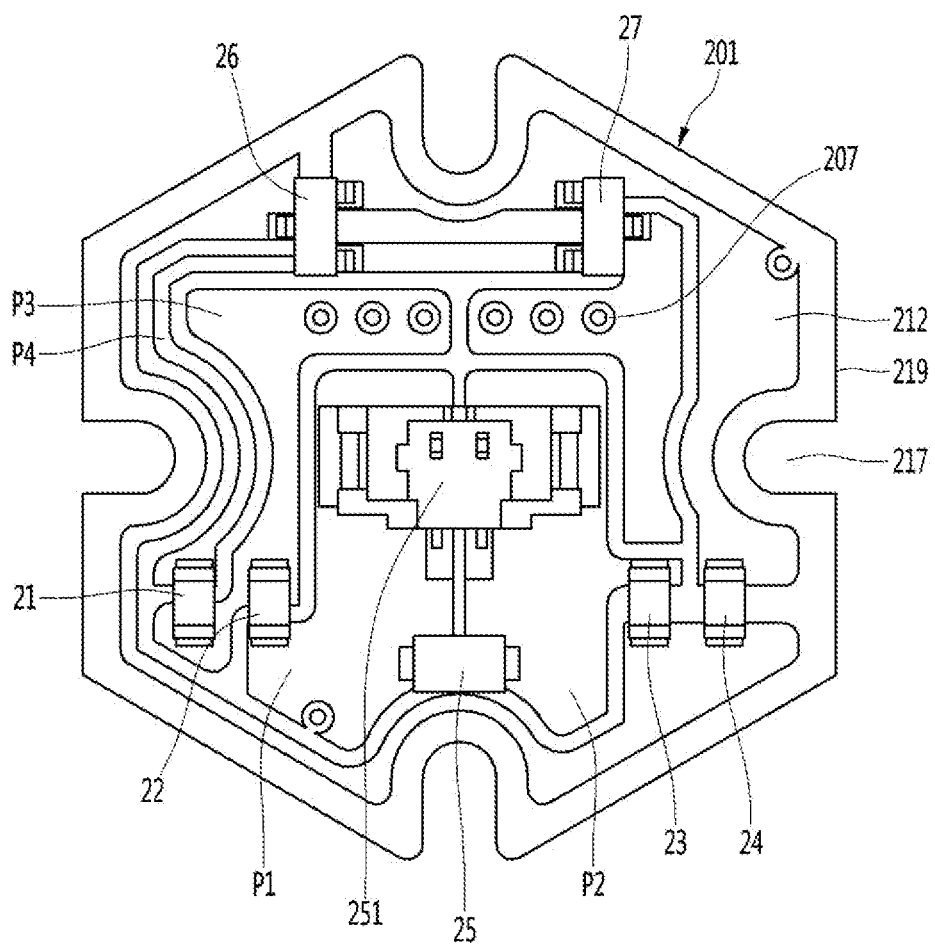
FIG. 5 is a rear view of the circuit board of FIG. 4.
Figure 6:
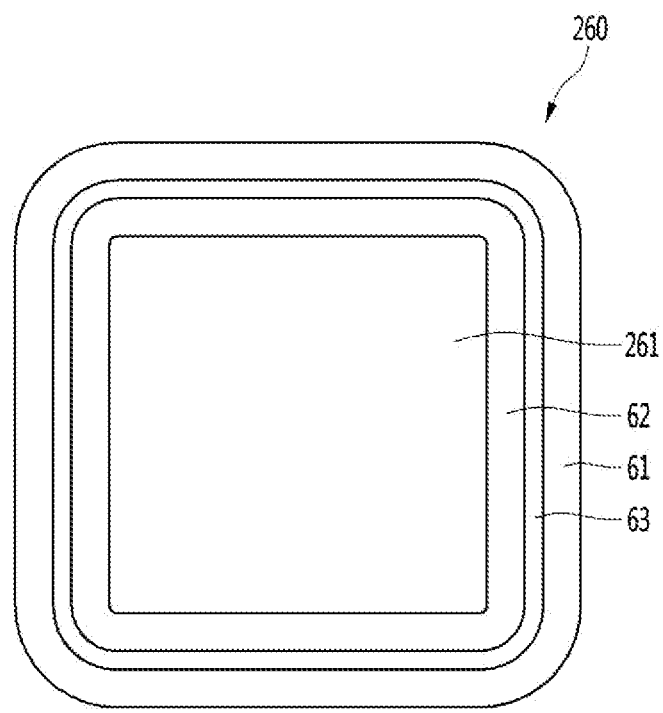
FIG. 6 is a plan view of the first gasket of FIG. 1.
Figure 7:
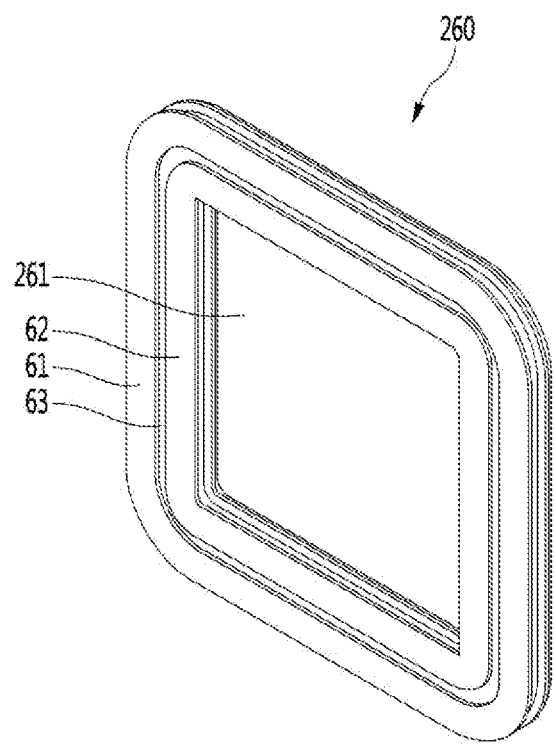
FIG. 7 is a perspective view of the first gasket of FIG. 6.
Figure 8:
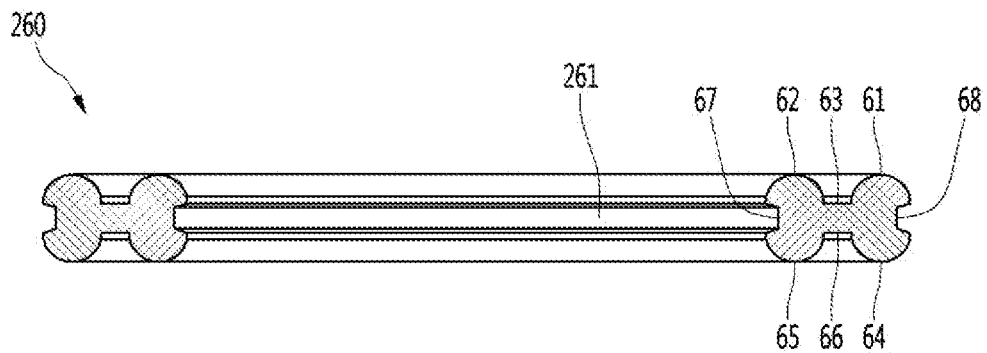
FIG. 8 is a side sectional view of the first gasket of FIG. 6.
Figure 9:
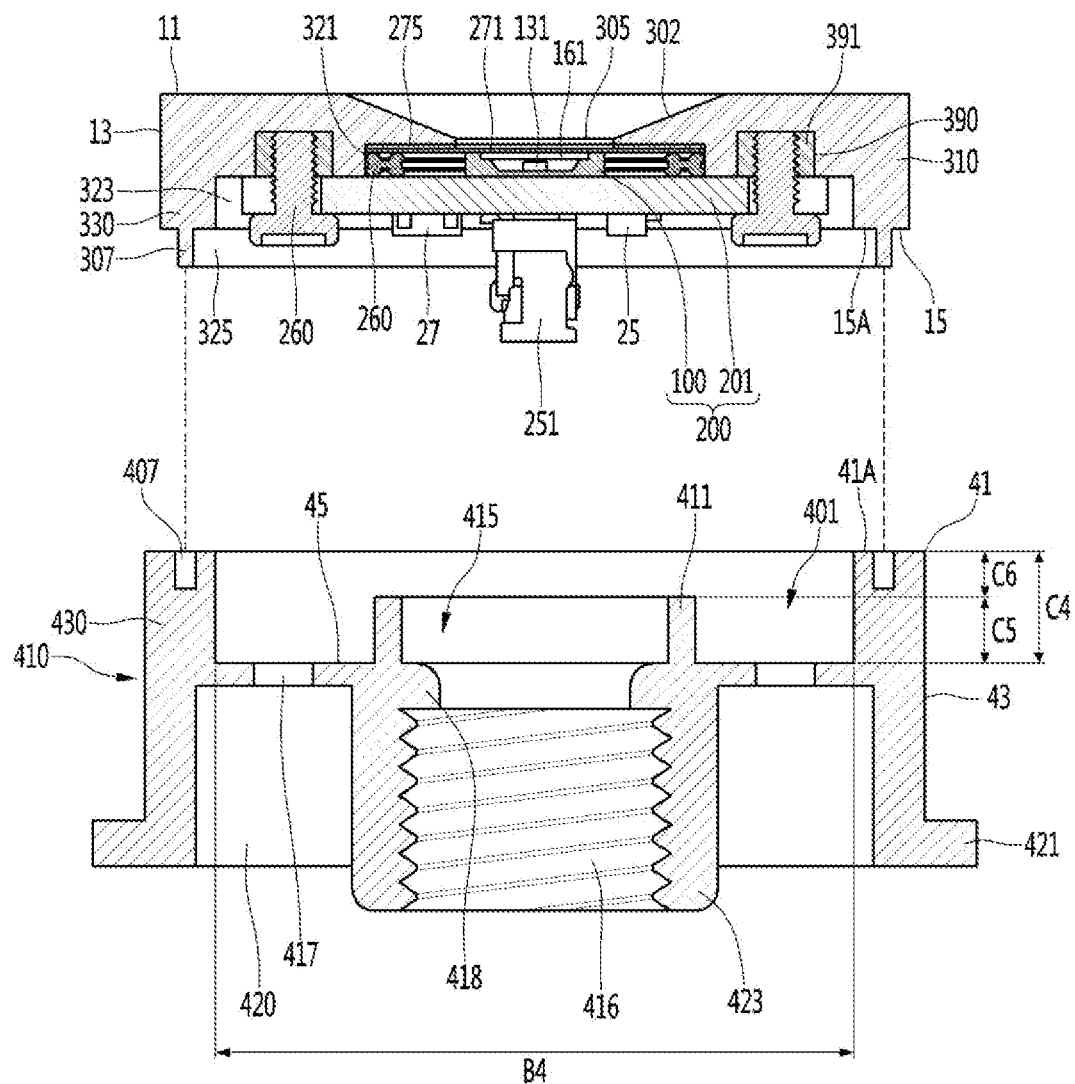
FIG. 9 is an exploded sectional view of the first cover and the second cover with which the light source module is coupled in FIG. 2.
Figure 10:
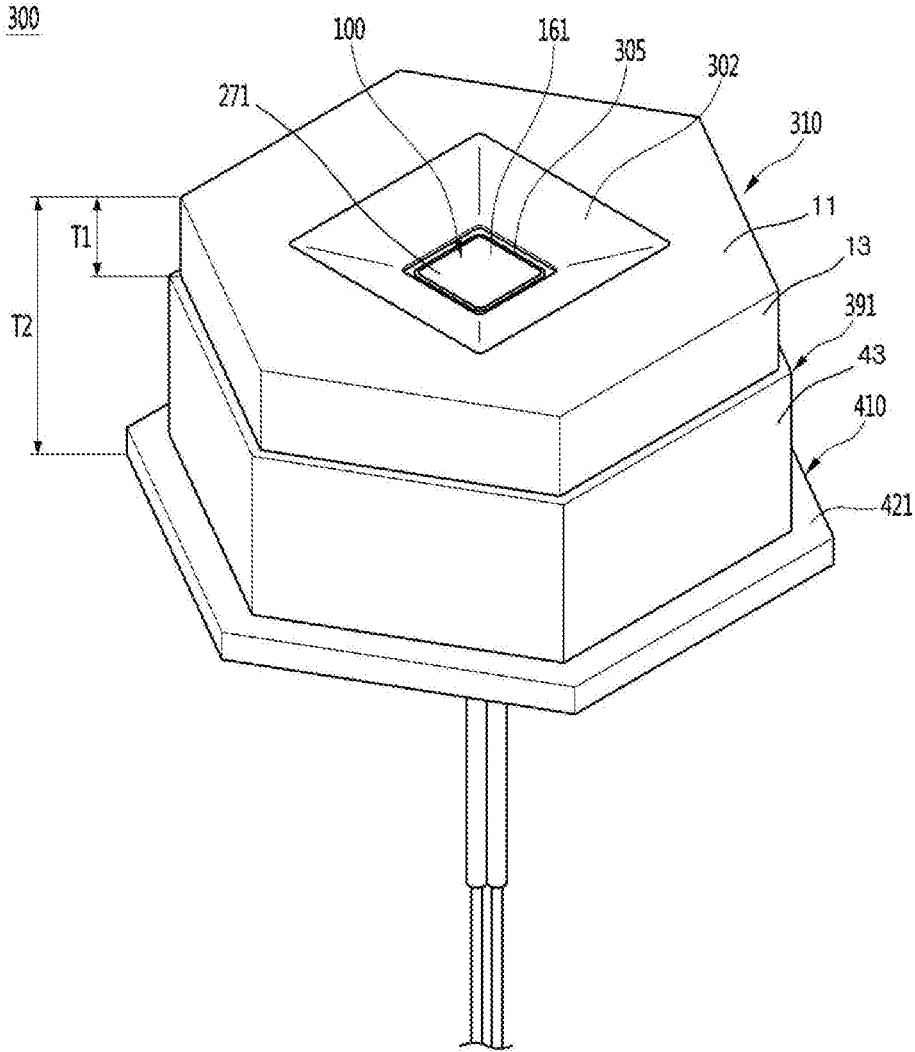
FIG. 10 is an assembled perspective view of the light source unit of FIG. 1.
Figure 11:
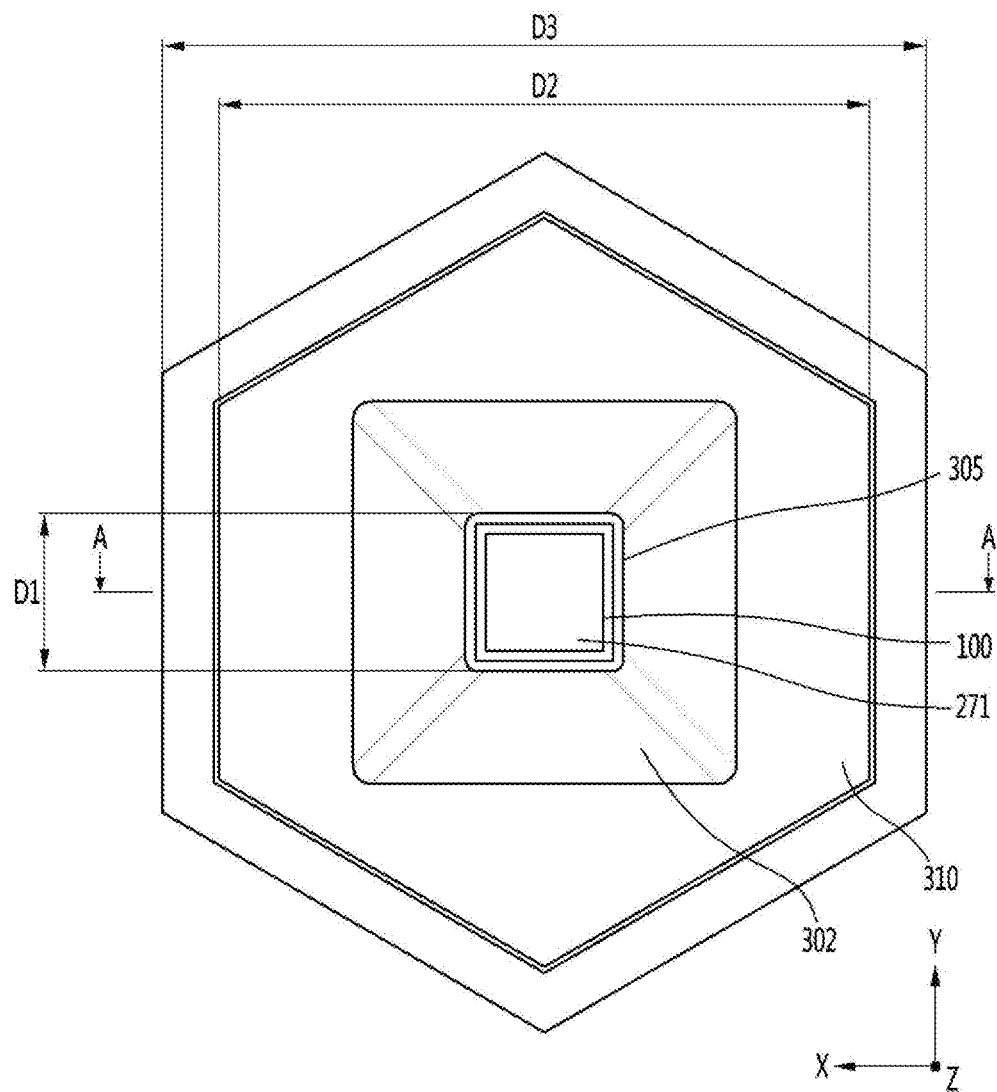
FIG. 11 is a plan view of the light source unit of FIG. 10.
Figure 12:
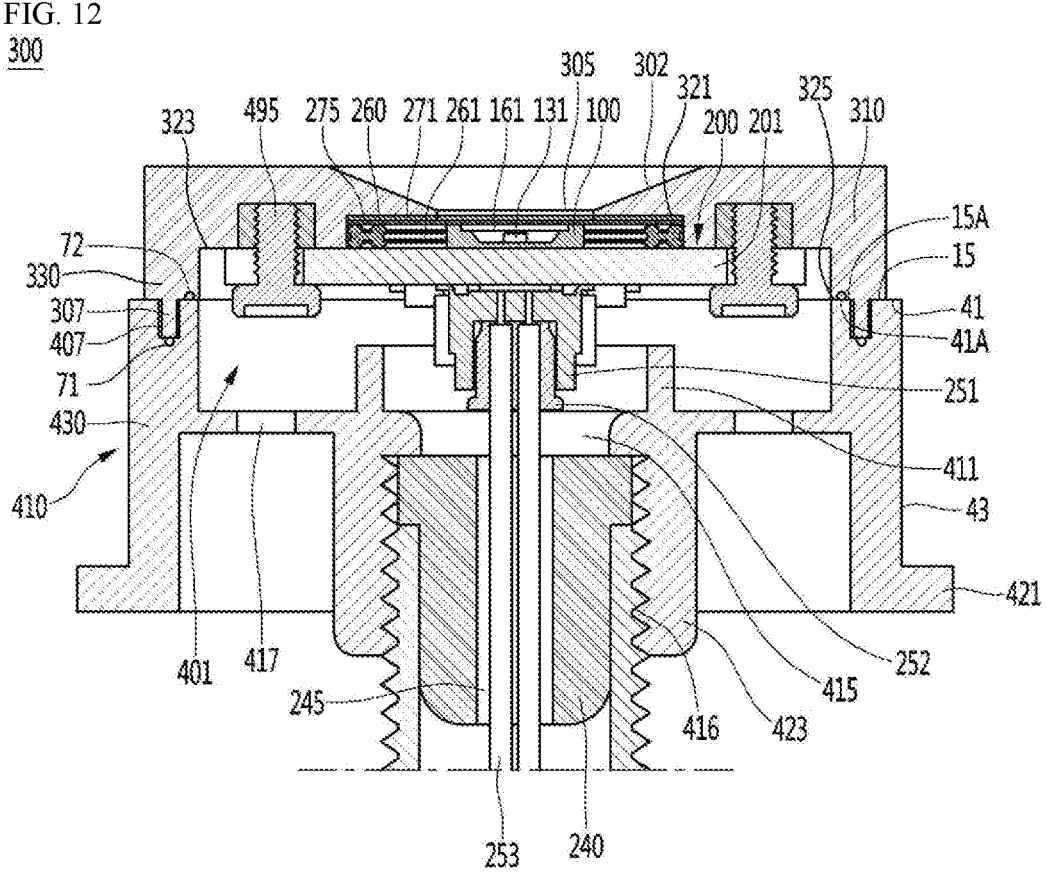
FIG. 12 is a cross-sectional view along line A-A of the light source unit of FIG. 11.
Figure 13:
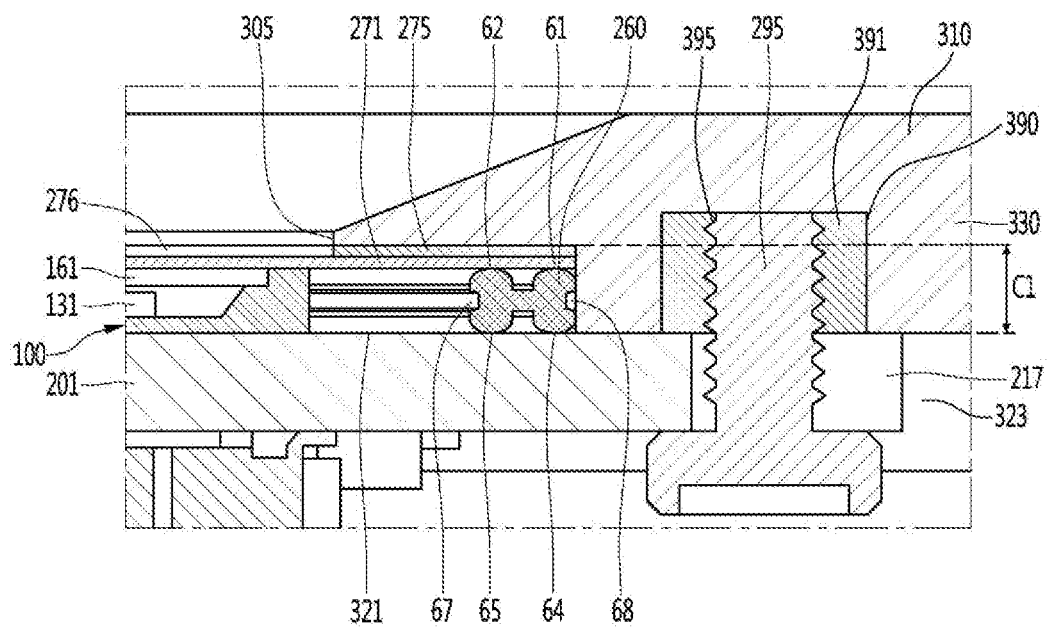
FIG. 13 is a partially enlarged view of the light source unit of FIG. 12 and a cross-sectional view showing a waterproof structure of the light source module.
Figure 14:
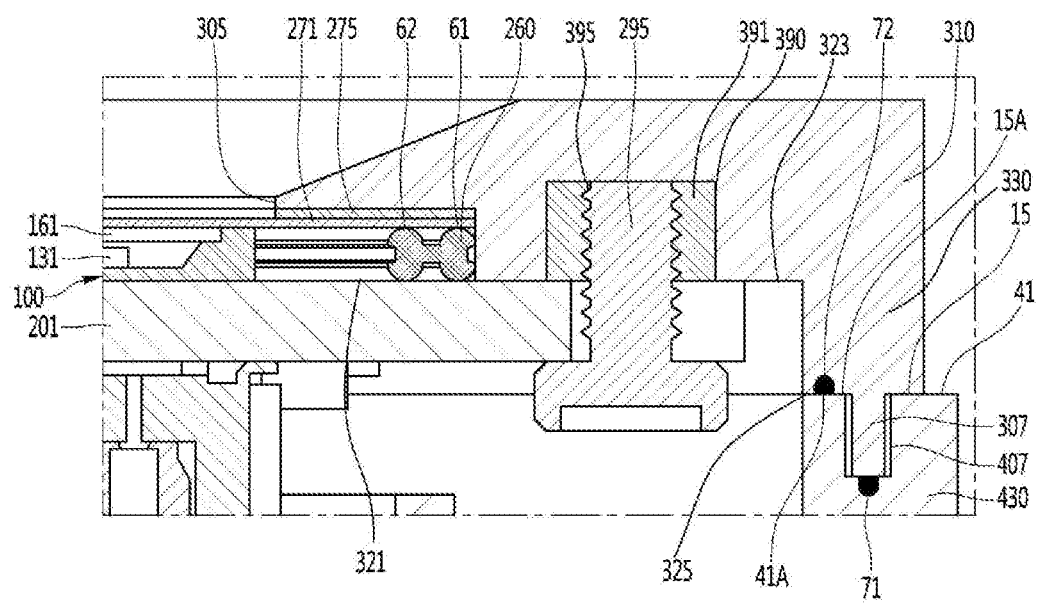
FIG. 14 is an enlarged view showing a waterproof member between the first and second covers of the light source unit of FIG. 12.

FIG. 1 is an exploded perspective view of a light source unit according to an embodiment of the invention, FIG. 2 is a side sectional view showing the exploded state of the light source unit of FIG. 1, FIG. 3 is a side cross-sectional view illustrating an example of coupling the first cover and the light source module of FIG. 2, FIG. 4 is a front view showing an example of a circuit board of the light source module of FIG. 1, FIG. 5 is a rear view of the circuit board of FIG. 4, FIG. 6 is a plan view of the first gasket of FIG. 1, FIG. 7 is a perspective view of the first gasket of FIG. 6, FIG. 8 is a side sectional view of the first gasket of FIG. 6, FIG. 9 is an exploded sectional view of the first cover and the second cover with which the light source module is coupled in FIG. 2, FIG. 10 is an assembled perspective view of the light source unit of FIG. 1, FIG. 11 is a plan view of the light source unit of FIG. 10, FIG. 12 is a cross-sectional view along line A-A of the light source unit of FIG. 11, FIG. 13 is a partially enlarged view of the light source unit of FIG. 12 and a cross-sectional view showing a waterproof structure of the light source module, and FIG. 14 is an enlarged view showing a waterproof member between the first and second covers of the light source unit of FIG. 12.

Referring to FIGS. 1 to 14, the light source unit 300 according to an embodiment of the present invention may include a light source module 200, a first cover 310, and a second cover 410. The light source module 200 may include a light emitting device 100 and a circuit board 201. The first cover 310 has an open region 305 through which light emitted from the light emitting device 100 is emitted and may cover an upper portion and a periphery of the light source module 200. The second cover 410 may be coupled to the first cover 310 to cover the lower portion of the light source module 200.

The light source unit 300 according to an embodiment of the present invention may include a waterproof member. The waterproof member may be disposed on at least one or two or more among an upper region of the light emitting device 100, an outer region of the light emitting device, a region between the circuit board 201 and the first cover 310. For example, the waterproof member may include a waterproof film 271 disposed on the light emitting device 100. The waterproof member may include first waterproof members 260 and 275 disposed along the outer circumference of the light emitting device 100 and closely contacted with the circuit board 201 and the first cover 310. The waterproof member of the light source unit 300 according to the embodiment of the present invention may include a second waterproof member (71 and 72 in FIG. 12) disposed around the periphery of the first and second covers 310 and 410. The light source unit 300 according to an embodiment of the present invention may include waterproof members of different kinds from each other. The waterproof members of different kinds from each other according to the embodiment of the present invention may be disposed in different regions.

The light source unit 300 includes a light source module 200 between the first and second covers 310 and 410, and an open region 305 where light is emitted and a boundary between the first and second covers 310 and 410 are waterproofed and may be provided as a sterilizing device in the reservoir water tank. The light source unit 300 draws out the signal cables 253 connected to the light source module 200 to supply power to the light source module 200. The light source unit 300 is used as a device for sterilizing an indoor unit of the refrigerator, an evaporator and a condensed water, a sterilizing device in the device such as an air washer, a sterilizing device of the water reservoir and a discharge water of a water purifier, or a sterilizing device in the inside of a toilet.

The light source module 200 may include a light emitting device 100 and a circuit board 201 disposed under the light emitting device 100. The light emitting devices 100 may be disposed on the circuit board 201 in a single or multiple layers. The light emitting device 100 of the light source module 200 may emit light having a wavelength within a range of ultraviolet to visible light. The light emitting device 100 may emit ultraviolet wavelength, for example. The ultraviolet wavelength may include a UV-C wavelength. The ultraviolet wavelength may be a wavelength of 400 nm or less, for example, 200 to 280 nm. One or a plurality of light emitting chips 100 may be disposed in the light emitting device 100.

The circuit board 201 may include a circuit pattern. The circuit board 201 may include at least one of a resin printed circuit board (PCB), a metal core PCB (MCPCB), a non-flexible PCB, a flexible PCB (FPCB), a ceramic PCB. The circuit board 201 may include a layer of a resin material or a layer of a ceramic material. The resin material may be a silicon, epoxy resin, a thermosetting resin including a plastic material, or a material having high heat resistance or high light resistance. The ceramic material includes a low temperature co-fired ceramic (LTCC) or a high temperature co-fired ceramic (HTCC) which is co-fired.

Referring to FIGS. 4 and 5, a plurality of via structures 207 may be formed in the circuit board 201. The via structure 207 may be selectively connected to a first circuit patterns 204 and 205 on an upper portion and an upper circuit patterns P1 and p2 under a lower portion. The via structure 207 may be provided to penetrate the circuit board 201 vertically. The first circuit patterns 204 and 205 may be electrically connected to the light emitting device 100. The second circuit patterns P1 and P2 may be electrically connected to the components 21, 22, 23, 24, 25, 26 and 27 through other connection patterns P3 and P4.

The components 22, 23, 24, 25, 26 and 27 disposed on the lower surface of the circuit board 201 include a plurality of resistors 21, 22, 23 and 24, a protection element 25, a transistor 26, and a voltage regulator 27. The components 22, 23, 24, 25, 26 and 27 may be selectively connected to the second circuit patterns P1 and P2 and the connection patterns P3 and P4. The components 22, 23, 24, 25, 26 and 27 may protect the light emitting device 100 and control the driving. A connector 251 connected to the second circuit patterns P1 and P2 may be connected to a lower portion of the circuit board 201 and the connector 251 may be connected through the second cover 410. By disposing the components 22, 23, 24, 25, 26 and 27 under the circuit board 201, a sealing region may be reduced when sealing the circuit board (201) for moisture proofing.

As shown in FIG. 4, a width D4 of the circuit board 201 in the first direction may be 30 mm or less, for example, in a range of 20 mm to 30 mm, when a top view shape of the circuit board 201 is polygonal, and a length D5 of one side of the circuit board 201 may be in a range of 10 mm or more, for example, 10 mm to 17 mm, when the top view shape of the circuit board 201 is a pentagonal shape. A size of the circuit board 201 may vary depending on a size of the light source unit 300 and the capacity of the reservoir water tank, but is not limited thereto.

The circuit board 201 may include a plurality of fastening holes 217. The fastening holes 217 may be separately arranged along the outer periphery of the circuit board 201. The fastening holes 217 may be recessed inwardly from the outer periphery of the circuit board 201, and may have a hemispherical shape or a polygonal shape. A metal layer 219 may be disposed in the fastening holes 217. The metal layer 219 may be disposed on a surface of the fastening holes 217 in order to relieve an impact transmitted to the circuit board 217 by an externally applied force. More than three or more than four fastening holes 217 of the circuit board 201 may be disposed, and the circuit board 201 may be pressed upward by a uniform force in an entire region.

As shown in FIGS. 2 and 3, the waterproof film 271 seals a surface of the light emitting device 100, for example, the upper surface of the light emitting device 100. The waterproof film 271 may be disposed between the first cover 310 and the light source module 200. The waterproof film 271 may be closely adhered to the upper surface of the light emitting device 100. The waterproof film 271 may be adhered to a transparent window 161 of the light emitting device 100 to transmit light. The outer portion of the waterproof film 271 may extend outside a region of the light emitting device 100 and may be disposed between the first and second gaskets 260 and 275 of the first waterproof member. An upper surface area of the waterproof film 271 may be larger than an upper surface area of the light emitting device 100. A width of the waterproof film 271 may be greater than the width of the light emitting device 100. The outer surface of the waterproof film 271 may face the upper surface of the circuit board 201 or be opposed to the upper surface of the circuit board 201.

The waterproof film 271 may include fluorine. The fluorine has a strong chemical bonding force with carbon and does not cause intermolecular bond breakdown due to ultraviolet ray. The waterproof film 271 may be defined as a fluororesin layer. The molecular chain of the waterproof film 271 is a helical structure. Since the structure of the molecular chain is a three-dimensional helical structure and thus fluorine atoms block surrounding of the carbon-carbon bond without intervals, the destruction of molecular chains due to penetration of ultraviolet ray and oxygen may be prevented. Also, the waterproof film 271 may protect the material since the waterproof film 271 may block penetration of moisture such as oxygen, water, or oil to the surface of the material as much as possible. The waterproof film 271 is made of a light transmitting material and transmits light emitted from the light emitting device 100 as.

The waterproof film 271 may be a fluororesin material and may be transmitted the light without being broken by the light emitted from the light emitting device 100. Thus the waterproof film 271 may use as at least one of polychlorotrifluoroethylene (PCTFE), Ethylene+Tetrafluoroethylene (ETFE), fluorinated ethylene propylene copolymer (FEP) and Perfluoroalkoxy (PFA). Here, transmittance the ultraviolet wavelength becomes higher in the order of PCTFE, ETFE, FEP, and PFA and moisture absorption rate at ultraviolet wavelength becomes higher in the order of PCTFE, FEP and PFA. The embodiment may be used as a moisture-proof layer using at least one of PCTFE, FEP and PFA.

A thickness of the waterproof film 271 may be 1 mm or less, for example, 0.1 mm or less, or in a range of 0.05 mm to 0.1 mm. If the thickness is larger than the above range, the light transmittance is low. The light transmittance of the waterproof film 271 may be 70% or more, for example, 70% to 95% of the wavelength emitted from the light emitting chip 131. If the transmittance is less than 70%, the optical reliability due to the decrease in function may be deteriorated. The light emitted from the light emitting chip 131 by the waterproof film 271 may be transmitted without damages.

Referring to FIGS. 2 and 3, the first cover 310 includes a concave portion 302 having an open region 305 and recesses 321 and 323 opened at the lower portion thereof. The first cover 310 covers an upper portion and outer peripheries of the light source module 100 disposed under the open region 305.

The concave portion 302 of the first cover 310 may be recessed lower than the upper surface 11 of the first cover 310. The bottom of the concave portion 302 may include a sloped surface from the upper surface 11 of the first cover 310 to the open region 305 or may include a curved surface having a predetermined curvature. The bottom of the concave portion 302 may include surfaces whose edge portions have a predetermined curvature. The concave portion 302 has a gradually lower depth toward a center portion thereof. As shown in FIG. 3, a depth C0 of the concave portion 302 may be equal to or less than a half of the thickness T1 of the first cover 310. As another example, the upper surface 11 of the first cover 310 may be disposed on a flat surface. As another example, an optical lens (not shown) may be disposed on the open region 305 of the first cover 310, and a material of the optical lens may include glass, silicon, or epoxy. The optical lens may comprise a convex hemispherical shape.

The open region 305 of the first cover 310 may be disposed at the bottom center of the concave portion 302. The open region 305 may be a region through which a center of the first cover 310 is vertically penetrated. The open region 305 may have an area of at least one times the area of the upper surface of the light emitting device 100, and may be, for example, more than 1 time, more than 2 times, or more than 1 time and less than 1.5 times. If the area of the open region 305 exceeds the above range, the area for waterproofing may be increased and the waterproof efficiency may be lowered.

The light emitting device 100 of the light source module 200 coupled between the first and second covers 310 and 410 may correspond to or protrude from the open region 305 of the first cover 310. An upper portion of the light emitting device 100 of the light source module 200 may protrude through the open region 305. The waterproof film 271 covering the upper surface of the light emitting device 100 may be exposed to the open region 305 without directly exposing the surface of the light emitting device 100. The open region 305 is disposed to be larger than the width or upper surface area of the light emitting device 100 and the waterproof film 271 is in close contact with the surface of the light emitting device 100 exposed to the open region 305, and the water penetrating through the open region 305 may be waterproof or moisture-proof. A part of the waterproof film 271 may protrude toward the upper surface 11 of the first cover 310 by the light emitting device 100. A part of the waterproof film 271 may protrude higher than the bottom of the open region 305 through the open region 305. The waterproof film 271 may be in contact with the side wall of the open region 305. In this case, since the waterproof film 271 contacts the open region 305, the waterproof effect may be improved.

An outer shape of the open region 305 may have the same shape as an outer shape of the light emitting device 100. The outer shape of the open region 305 may include a polygonal shape or a circular shape, but is not limited thereto. The outer shape of the light emitting device 100 may be polygonal or circular, but is not limited thereto. As show in FIG. 11, when the open region 305 may have a polygonal top view shape, the width D1 of one direction Y may be 10 mm or less, for example, in a range of 5 mm to 10 mm. The width D1 of the open region 305 may be in a range of 1/3.5 to 1/5.5 of the width D2 of one direction Y of the upper surface of the first cover 310. The open region 305 may have the same width in the first and second directions X and Y, or may be provided in either direction longer.

Referring to FIG. 3, the first cover 310 may include concave recesses 321 and 323 that are open at the bottom. The recesses 321 and 323 of the first cover 310 may include a first recess 321 in which the first waterproof members 260 and 275 are disposed and a second recess 323 in which the circuit board 201 is disposed. The first recess 321 may be disposed to overlap with the concave portion 302 in the vertical direction. The first recess 321 and the concave portion 302 may be disposed on opposite sides of a horizontal straight line at the bottom of the open region 305. The first recess 321 may be disposed at a width B1 that is narrower than an upper width D4 of the concave portion 302. This may prevent a size of the waterproof film 271 or the first waterproof members 260 and 275 from increasing. Also, the widths have a relation of D4>B1>D1 and may increase a path of the moisture-proof and waterproof.

The first recess 321 may have a bottom view shape in a polygonal or circular shape and may be a region where the light emitting device 100 is disposed and a peripheral region thereof. The depth C1 of the first recess 321 may be greater than the thickness of the light emitting device 100. The depth C1 of the first recess 321 is a depth based on a horizontal straight line of an upper surface of the second recess 323 and the depth C1 of the first recess 321 is an interval between the circuit board 201 and the upper surface (or ceiling) of the first recess 321. The depth C1 of the first recess 321 may be smaller than the sum of the thickness of the waterproof film 271 and the thickness of the first waterproof member 260 and 275. The depth C1 of the first recess 321 is smaller than the sum of the thickness of the waterproof film 271 and the thickness of the first waterproof members 260 and 275. Therefore, the waterproof film 271 and the first waterproofing members 260 and 275 may be compressed in an upward direction. A pressure applied by the resilient repulsive force of the waterproof film 271 and the first waterproof members 260 and 275 may be increased. The first recess 321 may be disposed to overlap with the concave portion 302 disposed on the upper portion of the first cover 310 in the vertical direction. The width or top surface area of the first recess 321 in the first direction may be smaller than a width or area of the concave portion 302 in the first direction.

The waterproof film 271 and the first waterproof members 260 and 275 may be disposed in the first recess 321. As shown in FIGS. 3 and 9, the first waterproof members 260 and 275 may include a plurality of gaskets, for example, a first gasket 260 and a second gasket 275, disposed around the waterproof film 271. The first waterproof member 260 and 275 may include a multi-layered gasket. The first waterproof member 260 and 275 may include a vertically stacked double gasket. The first gasket 260 may have a first opening 261 into which the light emitting device 100 is inserted and may be disposed between the circuit board 201 and the waterproof film 271. The second gasket 275 has a second opening 276 for opening the upper surface of the light emitting device 100 and is disposed between the waterproof film 271 and the first recess 321 of the first cover 310. The first gasket 260 is disposed between the lower surface of the waterproof film 271 and the upper surface of the circuit board 201 and the second gasket 275 is disposed between the upper surface of the waterproof film 271 and an upper surface of the first recess 321.

The light emitting device 100 may be inserted into the first opening 261 of the first gasket 260. The first opening 261 may be opened vertically in a thickness direction of the first gasket 260 and the upper surface of the circuit board 201 may be exposed to the first opening 261. An area of the first opening 261 may be no more than twice the area of the upper surface of the light emitting device 100, for example, more than 1 times and not more than 1.5 times. When the area of the first opening 261 exceeds twice the area of the light emitting device 100, a moisture-proof effect on a region of the first opening 261 exposed between the light emitting device 100 and the first gasket 260 may be deteriorated, and the thickness of the waterproof film 271 may be increased, thereby decreasing the light-transmitting efficiency. The top view shape of the first opening 261 may be polygonal or may have the same shape as the outer shape of the light emitting device 100. If the outer shape of the first opening 261 and the light emitting device 100 are the same, the outside of the waterproof film 271 may be prevented from being stuck.

The thickness of the first gasket 260 may be greater than the thickness of the light emitting device 100. The first gasket 260 may have a thickness of 2 mm or less, for example, in a range of 1.3 mm to 2 mm, or in a range of 1.2 mm to 1.7 mm. If the thickness is larger than the above range, the improvement of waterproof efficiency may be insignificant. If the thickness is smaller than the above range, an elastic repulsive force may be lowered and an adhesion with the waterproof film 271 may be lowered. The first gasket 260 may include a resin material having elasticity. The first gasket 260 may be NBR (Nitrile Butadiene Rubber), EPDM (Ethylene Propylene), or a resin material such as silicone. The first gasket 260 may be formed of a fluorine-based rubber. The first gasket 260 may use at least one of PCTFE (Polychlorotrifluoroethylene), ETFE (Ethylene+Tetrafluoroethylene), FEP (Fluorinated ethylene propylene copoly-mer), or PFA (Perfluoroalkoxy). The first gasket 260 made of fluorine may have improved heat resistance, chemical resistance, and abrasion resistance.

As shown in FIGS. 6 to 8, the first gasket 260 has a first concave region 63 between upper protrusions 61 and 62 and a second concave region 66 between lower protrusions 64 and 65. Since the upper protrusions 61 and 62 and the lower protrusions 64 and 65 are compressed when the first gasket 260 is compressed, an area of adhesion with other components may be increased. The upper protrusions 61 and 62 and the lower protrusions 64 and 65 of the first gasket 260 may be arranged to overlap each other in the vertical direction. The upper protrusions 61 and 62 and the lower protrusions 64 and 65 of the first gasket 260 may be compressed or contracted in the vertical direction by an external force. The first gasket 260 may include an inner groove 67 and an outer groove 68. When the first gasket 260 is compressed in the vertical direction, the upper protrusions 61 and 62 and the lower protrusions 64 and 65 may be further compressed in the horizontal direction. The outer groove 68 may be disposed to be concave in the direction of the light emitting device along a periphery between a first protrusion 61 located outside the upper protrusions 61 and 62 of the first gasket 260 and a third protrusion 64 located outside the lower protrusions 64 and 65. The inner groove 67 may be disposed to be concave in direction of an outer groove (68) along an periphery between a second protrusion 62 located inside the upper protrusions 61 and 62 of the first gasket 260 and a fourth protrusion 65 located inside the lower protrusions 64 and 65. The outer groove 68 and the inner groove 67 may be arranged so as to overlap in the horizontal direction.

The first gasket 260 may be disposed along the periphery of the first opening 261 and the protrusions 61, 62, 64 and 65 have a ring shape. Since the ring-shaped protrusions 61, 62, 64 and 65 of the first gasket 260 are disposed in the X-shape in cross section, it is possible to provide a double-contact effect on the upper and lower surfaces of the first gasket 260 and the waterproof efficiency may be improved. The first gasket 260 is disposed in the first recess 321 between the circuit board 201 and the lower surface of the waterproof film 271 so that the circuit board 201 is fastened as shown in FIG. 9 and the first gasket 260 may be compressed. When the first gasket 260 is compressed, the first gasket 260 is closely contacted between the waterproof film 271 and the circuit board 201 to seal the outer region of the light emitting device 100. Accordingly, the first gasket 260 may block moisture or water penetrating through the periphery of the light emitting device 100.

As shown in FIGS. 3 and 9, the second gasket 275 is disposed between the upper surface of the waterproof film 271 and the upper surface of the first recess 321, and may be in surface contact between the upper surfaces of the second recess 323 and the waterproof film 271. The second gasket 275 may include a second opening 276 and the second opening 276 may have an area smaller than the area of the first opening 261. The second opening 276 may have a larger area than the upper surface area of the light emitting device 100 or may be disposed outside an exit surface of the light emitting device 100, that is, the transparent window 161, and may be prevented interference with the emitted light.

Figure 18:
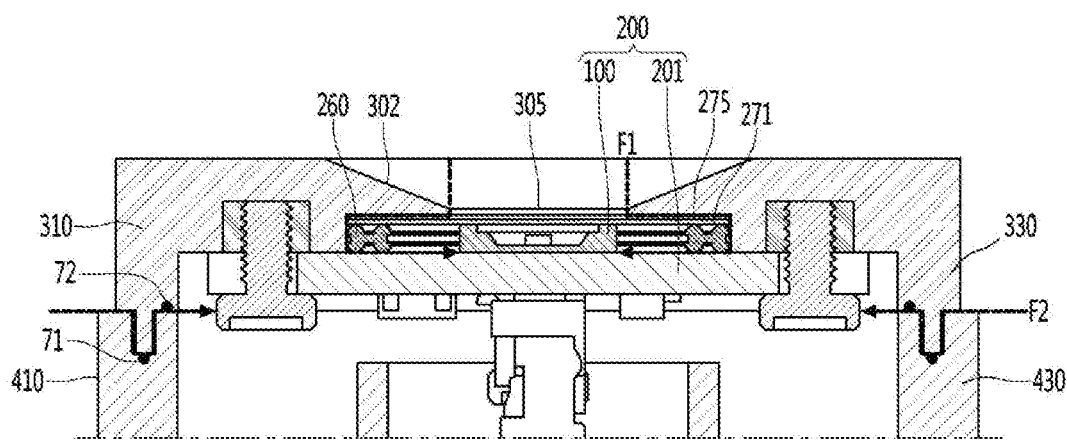
FIG. 18 is a view for explaining a waterproof cutoff path in a light source unit according to an embodiment of the present invention.

The second opening 276 may be disposed to have an area larger than that of the open region 305. The second opening 276 may prevent the second gasket 275 from being exposed through the open region 305. The width of the second opening 276 in the first direction may be greater than the width of the light emitting device 100 in the first direction and the width of the open region in the first direction. A contact area between the second gasket 275 and the first gasket 260 may be smaller than a contact area between the second gasket 275 and the upper surface of the first recess 321. The second gasket 275 may block moisture or water penetrating through the open region 305 and the first gasket 260 may be block moisture or water penetrating through an interface between the upper surface of the circuit board 201 and the first gasket 260. Since the upper surface of the first gasket 260 is in close contact with the waterproof film 271 and the lower surface of the first gasket 260 is in close contact with the upper surface of the circuit board 201, the waterproof effect in the lateral direction may be provided. That is, as shown in FIG. 18, the path of moisture or water penetrating through the penetration path F1 may be blocked.

The thickness of the second gasket 275 may be greater than the thickness of the waterproof film 271, and may be, for example, at least twice the thickness of the waterproof film 271. The thickness of the second gasket 275 may be in a range of 0.5 mm or less, for example, 0.1 mm to 0.5 mm. When the thickness of the second gasket 275 is larger than the above range, an adhesion or a waterproof efficiency between the second gasket 275 and the waterproof film 271, the adhesion between the second gasket 275 and the first cover 310 may be lowered, and when it is thinner than the above range, a stiffness may be lowered. An air tightness between the second gasket 275 and the upper surface of the waterproof film 271 and the first recess 321 may be maximized by setting the thickness of the second gasket 275 to 0.5 mm or less.

The second gasket 275 may include a resin material having elasticity. The second gasket 275 may be made of a resin material such as NBR (Nitrile Butadiene Rubber), EPDM (Ethylene Propylene), or a silicone. The second gasket 275 may be formed of a fluorine-based rubber material. The second gasket 275 may be at least one of PCTFE (polychlorotrifluoroethylene), ETFE (Ethylene+Tetrafluoroethylene), FEP (fluorinated ethylene propylene copolymer), and PFA (Perfluoroalkoxy). The second gasket 275 made of fluorine may be improved in heat resistance, chemical resistance, and abrasion resistance. The first gasket 260 and the second gasket 275 may be made of different materials or may be made of the same material. The first gasket 260, the second gasket 275, and the waterproof film 271 are formed of a fluorine material, thereby maximizing the waterproof property.

The second recess 323 of the first cover 310 may have a width B2 that is larger than the width B1 of the first recess 321 and is open at the bottom. The width B2 of the second recess 323 in the first direction may be larger than the width of the circuit board 201. The depth C2 of the second recess 323 may be an interval between the bottom of the first recess 321 and the bottom of the second recess 323. The depth C2 of the second recess 323 may be greater than or equal to the thickness of the circuit board 201, for example, greater than the thickness of the circuit board 201. A metal layer (219 in FIG. 4) is formed around the circuit board 201 to secure stiffness and to prevent damage to the circuit board 201 when the fastening member 495 is coupled. As shown in FIGS. 4 and 5, the metal layer 219 may be disposed around the upper surface, a side surface, and a lower surface of the circuit board 201. At least three or four fastening holes 217 of the circuit board 201 is disposed, and the circuit board 201 may be pressed upward by a uniform force in an entire area.

A bottom view shape of the second recess 323 may have a polygonal shape or a circular shape. The bottom view shape of the second recess 323 may be the same as the outer shape of the circuit board 201. As shown in FIGS. 4 and 5, the outer shape of the circuit board 201 may have a shape of rectangular or more, for example, a hexagonal shape, and may be provided in a pentagonal or octagonal shape as another example. As shown in FIG. 12, a fastening portions of the fastening members 495 may be inserted into the plurality of fastening holes 217 disposed around the outer periphery of the circuit board 201 and fastened to first covers 310 to be coupled. A plurality of fastening support portions 391 may be disposed around the outer periphery of the first recess 321. The fastening support portion 391 may be filled with a material different from that of the first cover 310 in the fastening hole 390 connected through the second recess 323. The fastening portion of the fastening member 495 may be fastened to the fastening support portion 391. When the fastening member 495 is a bolt, a hole 395 having a screw thread may be disposed in the fastening support portion 391, and a stepped structure may be disposed in a case of a rivet. When the fastening member 495 is a bolt, the fastening portion may be a tail having the screw thread, and a head portion of the fastening member 495 may be formed to a receiving region 401 of the second cover 410 at a lower portion of the circuit board 201.

As shown in FIGS. 9 and 12, the first gasket 260, the waterproof film 271, and the second gasket 275 are in close contact with the circuit board 201. At this time, the fastening member 495 may be fastened through the fastening hole 217 of the circuit board 201 and the fastening support portion 391 disposed on the second recess 323 of the first cover 310. In this case, the circuit board 201 may be closely attached to the first cover 310 by fastening the fastening member 495 while pushing the circuit board 201 upward under the circuit board 201. At this time, when the fastening member 495 is fastened to the circuit board 201 and the first cover 310, and the first gasket 260, the waterproof film 271, and the second gasket 275 may be closely contacted by the fastening member 495. Since the first gasket 260, the waterproof film 271 and the second gasket 275 are closely contacted between the circuit board 201 and the upper surface of the first recess 321, a moisture or a water penetrating may be blocked. In addition to, the fastening member 495 is fastened to the first cover 310 so that the first cover 310 and the circuit board 201 are brought into close contact with each other and the second gasket 275 and the first cover 310 are brought into close contact with each other, and a moisture and water penetrating through the open area 305 may be blocked.

As shown in FIGS. 13 and 14, when the fastening member 495 is fastened to the first cover 310 through the circuit board 201, the upper surface of the circuit board 201 is in close contact with the upper surface of the second recess 323. At this time, the circuit board 201 upwardly presses the first gasket 260, the waterproof film 271 and the second gasket 275 disposed in the first recess 321 and 260, the waterproof film 271 and the second gasket 275 may be pressed to the height C1 of the first recess 321. This is because at least one or both of the first and second gaskets 260 and 275 are formed by pressing the circuit board 201 such that a sum of the thicknesses of the first gasket 260, the waterproof film 271 and the second gasket 275 may be reduced or compressed. The rate at which the thicknesses of the first gasket 260, the waterproof film 271 and the second gasket 275 are compressed may be 30% or less, for example, in the range of 10% to 30%. The thickness to be compressed based on the sum of the thicknesses of the first gasket 260, the waterproof film 271 and the second gasket 275 may be in a range of 0.6 mm or less, for example, 0.3 mm to 0.6 mm. As shown in FIG. 9, the first cover 310 may include a first outer wall 330 around the lower portion thereof and the first outer wall 330 may cover the outer periphery of the second recess 323. As shown in FIG. 3, a straight line distance B3 between the opposite first outer walls 330 from each other may be greater than the width B2 of the second recess 323, and a straight distance B3 between the opposite outer side walls 330 from each other in FIG. 2. A height C3 of the first outer wall 330 may be equal to or less than the depth C2 of the second recess 323. The height C3 of the first outer wall 330 may be in a range of 1.2 mm or more, for example, 1.2 mm to 2 mm. When the height C3 of the first outer wall 330 exceeds the above range, the stiffness of the first and second covers 310 and 410 is lowered and a thickness of an optical unit (T2 of FIG. 10) may be increased, when the height C3 is smaller, the bonding strength between the first and second covers 310 and 410 may be reduced.

The second cover 410 may include a second outer wall 430 around the upper portion. The second outer wall 430 may be disposed along the outer periphery of the receiving region 401 and protrude toward the first cover 310. Here, the area of the upper surface 41 of the second cover 410 may be larger than the area of the lower surface 15 of the first cover 310. As shown in FIG. 11, a width D3 of the second cover 410 in one direction X may be greater than a width D2 of the first cover 310. In this case, the outer side wall of the second cover 410 may protrude outward from the outer side wall of the first cover 310.

The first and second covers 310 and 410 may be formed of glass, plastic, polypropylene (PP), polyethylene (PE), polycarbonate (PC), polybutylene terephthalate (PBT), POM (Poly $O_{xy}$ Methylene, Polyacetal), PPO (polyphenylene oxide) resin, or modified PPO resin. Here, modified PPO (Modified PPO) resin includes a resin in which PPO is mixed with a resin such as PS (polystyrene) or polyamide (PA) series, and has heat resistance and maintains property stably even at low temperature. At least one or both of the first and second covers 310 and 410 may provide a surface white color. As another example, the second cover 410 may be made of metal, but is not limited thereto. As another example, the first and second covers 310 and 410 may be made of metal and are not limited thereto. The outer shape of the first and second covers 310 and 410 may be a polygonal shape or a circular shape in a top view shape, but is not limited thereto.

Meanwhile, when the first cover 310 is coupled to the light source module 200 therein and is coupled to the second cover 410 in correspondence with each other, the light source module 300 may be provided as shown in FIG. 10. The thickness T2 of the light source unit 300 may be provided in a slim size in a range of 50 mm or less, for example, 20 mm to 30 mm.

When the light source module 200 is coupled to the first cover 310 and the second cover 410 is coupled to the first cover 30 in correspondence with each other, the first and second covers 310 and 410 are bonded together by the second waterproof member. As shown in FIG. 12, the second waterproof member may include bonding potions 71 and 72 bonded to each other along the outer peripheries of the first and second covers 310 and 410. At least one of the second waterproof members may be disposed on a bonding structure that is formed along the outer walls 330 and 430 of the first and second covers 310 and 410.

As shown in FIGS. 12 and 14, the first and second covers 310 and 410 combine with each other to be waterproofed, for example, when the first cover 310 may have protrusions 307 to an outer periphery of the first cover 310, the second cover 410 may have grooves 407 around a region where the protrusion 307 is inserted, for example, to an outer periphery of the second cover 410. Conversely, when the first cover 310 has a groove along the periphery, the second cover 410 may include a protrusion that is inserted into the groove of the first cover 310. The combined structures of the first and second covers 310 and 410 may be disposed on the first and second outer walls 330 and 430. The combined structures may be continuously disposed along the first and second outer walls 330 and 430. A single combined structure having a single protrusion and groove to be combined therewith, or a double-combined structure having a double protrusion and a double groove. Below, for convenience of description, the protrusion 307 is disposed under the first outer wall 330 of the first cover 310 and the groove 407 is disposed under the second outer wall 430 of the second cover 410, and will be described as an example of a single combined structure.

A protrusion 307 is protruded from the lower portion of the first outer wall 330. The protrusion 307 is continuously connected along the first outer wall 330 and protruded toward the second cover 410. The protrusion 307 may include a polygonal ring shape or a circular ring shape. The protrusion 307 may protrude downward from a region spaced apart from the outer side and the inner side of the first outer wall 330, for example, from the center region.

The outer region of the protrusion 307 of the lower surface of the first outer wall 330 corresponds to an outside of an upper surface of the second outer wall 430 of the second cover 410 and the inner region of the protrusion 307 corresponds to an inside of the upper surface of the second outer wall 430.

The second waterproof member may be disposed in a region where the first and second outer walls 330 and 430 face each other, and may include a single bonding structure or a double bonding structure. In the case of the double bonding structure, since they are arranged in different regions, the effect of blocking moisture and water may be increased. The double bonding structures are disposed at different heights, respectively, to provide a long moisture penetration path and to maximize the moisture-proof/waterproof effect.

The double bonding structure may include a bonding portion formed of at least one or all of the materials of the first and second covers 310 and 410. The first and second covers 310 and 410 may be a part of a fusion-bonding to each other. At least one or both of the first outer wall 330 of the first cover 310 and the second outer wall 430 of the second cover 410 may include the bonding portions 71 and 72. The bonding portions 71 and 72 may be bonded between the first outer wall 330 of the first cover 310 and the second outer wall 430 of the second cover 410.

The bonding portions 71 and 72 may include a first bonding portion 71 bonded between the protrusion 307 of the first cover 310 and the groove 407 of the second cover 410, and a second bonding portion 72 bonded along the inner periphery of the outer wall 330 and the second outer wall 430. A merged portion of the first bonding portion 71 may include at least one or both materials of the first and second outer walls 330 and 430 of the first and second covers 310 and 410. The size or height of the first bonding portion 71 may be in the range of 0.1 mm or more, for example, 0.1 mm to 0.5 mm in the vertical direction. The merged portion of the second bonding portion 72 may include at least one or both of the first and second outer walls 330 and 430 of the first and second covers 310 and 410. The size or height of the second bonding portion 72 may be in the range of 0.1 mm or more, for example, 0.1 mm to 0.5 mm in the vertical direction.

A position of the first bonding portion 71 may be lower than a position of the second bonding portion 72 and may be disposed outside of the second bonding portion 72. The first and second bonding portions 71 and 72 may be bonded at different heights and different positions in a region between the first and second outer walls 330 and 430. The maximum distance between the first bonding portions 71 may be greater than the maximum distance between the second bonding portions 72. The first and second bonding portions 71 and 72 may not use an additional adhesive and may not process complex bonding work, as a two facing portions of the first and second covers 310 and 410 are merged by the ultrasonic process. When the ultrasonic process, for example, irradiation of the joint of the first and second covers 310 and 410 may generate momentary friction at the two joint faces, which may combine the joint of the first and second covers 310 and 410 to create a strong molecular bond. The first and second bonding portions 71 and 72 may be disposed in an inner region spaced apart from the outer surface of the first and second covers 310 and 410. The first and second bonding portions 71 and 72 do not deform or deteriorate the outer surfaces of the first and second covers 310 and 410 and may provide a clean appearance. The merged surfaces of the first and second covers 310 and 410 are firmly coupled to each other through molecular bonding, thereby improving the moisture-proof and waterproof efficiency. That is, moisture or water penetrating through the path F2 in FIG. 18 may be blocked.

As shown in FIGS. 9 and 12, the second cover 410 may include a cable hole 415 and a connector guide portion 423 protruding in a lower direction. The connector 251 connected to the signal cable 253 may be inserted through the connector guide portion 423 and the cable hole 415 and connected to the circuit board 201. A plurality of signal cables 253 may be connected to the connector 251, and the signal cable 253 may be protected by a protective sheath and may include a power cable. A signal cable 253 may be inserted into the inner hole 245 of the cable gasket 240. A cable gasket 240 is coupled to the outer periphery of the signal cable 253 and the width or diameter of the upper portion (241 in FIG. 1) of the cable gasket 240 may be greater than the width or diameter of the lower portion 243. The cable gasket 240 may be coupled or fixed to the inside of the cable hole 417. The outer surface of the cable gasket 240 may be free of screw and may be formed of plastic or resin. The connector 251 may be spaced apart from the cable gasket 240. The upper portion (241 in FIG. 1) of the cable gasket 240 is coupled through the connector guide portion 423 of the second cover 410 and may be caught on a locking protrusion 418 protruding inward from the upper portion of the connector guide portion 423, limiting the upper movement or adhering closely to the reservoir water tank. The cable gasket 240 may be in contact with two or more screw (416 in FIG. 12) of the connector guide portion 423. A coupling member such as a nut of a reservoir water tank may be coupled to a lower screw of the connector guide portion 423.

The locking protrusion 418 protruding inward is disposed on the upper portion of the cable hole 415. The locking protrusion 418 restricts the insertion of the cable gasket 420 and may be in contact with a top surface of the cable gasket 240.

Figure 16:
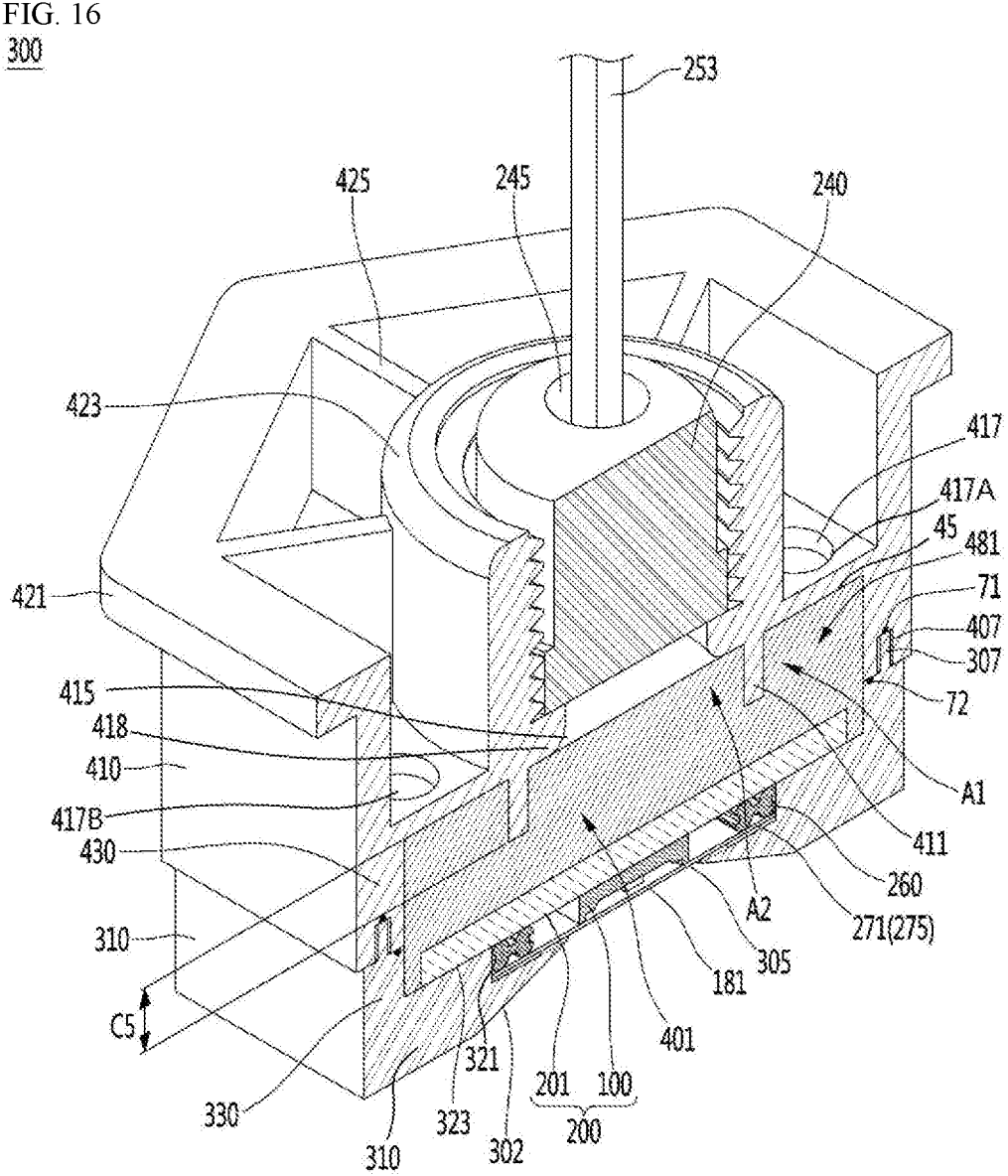
FIG. 16 is a side sectional view showing a molding member sealed between the first and second covers in the light source unit of FIG. 15.

As shown in FIG. 16, the receiving region 401 of the second cover 410 may include a molding member 481. The molding member 481 may be in contact with the upper surface and the outer surface of the second recess 323 through the side surface of the circuit board 201. The molding member 481 seals between the circuit board 201 and the second recess 323 of the first cover 310. The molding member 481 seals a region between the surface of the circuit board 201 and the receiving region 401. The molding member 481 may be in non-contact with the connector guide portion 423.

Figure 15:
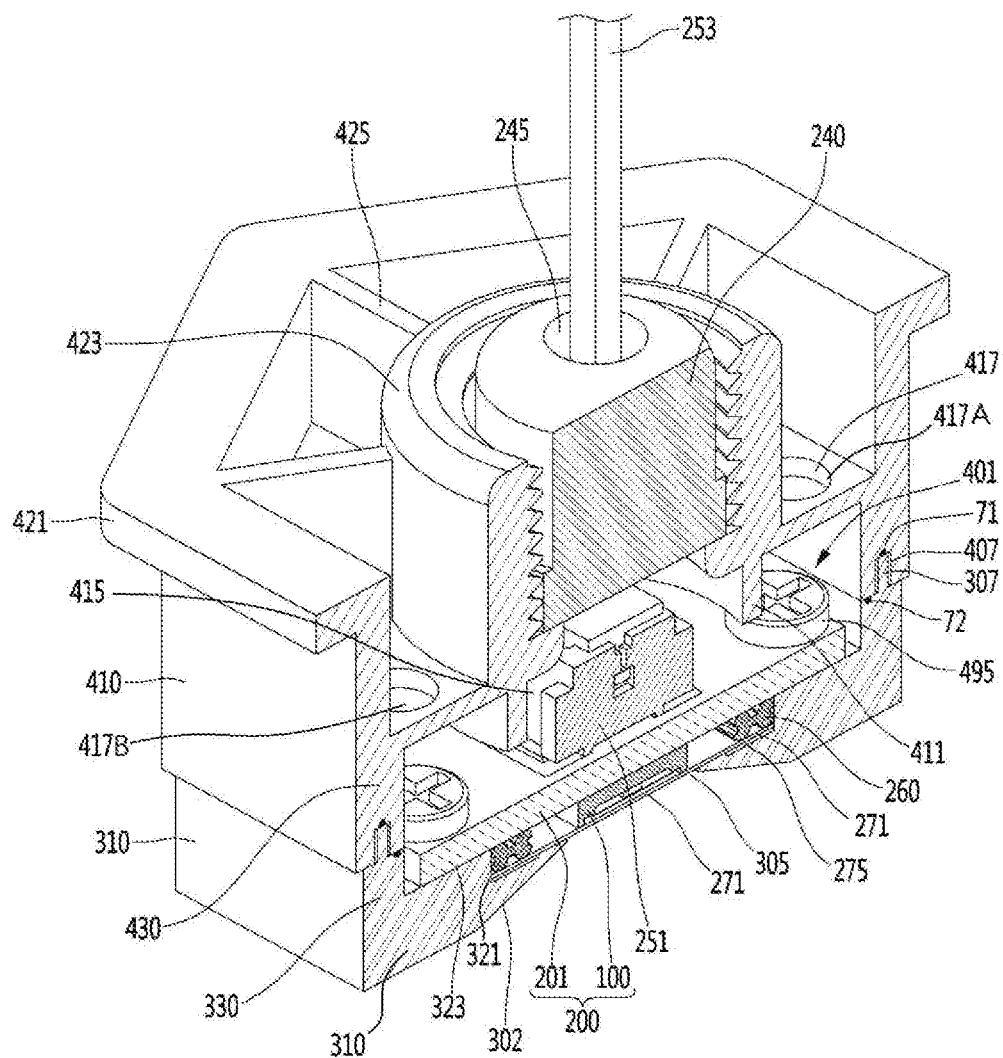
FIG. 15 is a side sectional view as seen from the back side of the light source unit of FIG. 12.

As shown in FIGS. 15 and 16, the molding member 481 is molded in the receiving region 401 of the second cover 410, and may be sealed a bonding portion of the first and second covers 310 and 410, for example, the boundary region between the outer wall 330 and the second outer wall 430, and a penetration path of moisture or water through a space between the first and second outer walls 330 and 430 may be long.

The molding member 481 contacts the sub gasket 252 coupled to the connector 251 shown in FIG. 12 and seals the space between the connector 251 and the molding member 481. The sub gaskets 252 may be closely coupled between the connector 251 and the signal cable 253. The molding member 481 may seal a periphery of the sub gaskets 252 that are in close contact with the signal cable 253. Accordingly, a region where the connector 251 is coupled at the bottom of the circuit board 201 is sealed to prevent moisture and water from penetrating.

The molding member 481 may seal the surface of the fastening member 495 coupled to the circuit board 201. The molding member 481 may include a material such as silicon or epoxy, but is not limited thereto.

As shown in FIGS. 2 and 9, a guide protrusion 411 is disposed on an outer periphery of the connector 251 and disposed to an upper portion of the cable hole 415, and the guide protrusion 411 is formed in a ring shape. The ring shape may include a circular shape or a polygonal shape. The guide protrusion 411 may protrude from a bottom 45 of the receiving region 401 of the second cover 410 to a predetermined height. The guide protrusion 411 may be disposed lower than the first outer wall 330 of the first cover 310 and higher than the bottom 45 of the receiving region 401 of the second cover 410. As shown in FIG. 9, the guide protrusion 411 may protrude from the receiving region 401 toward the circuit board 201. The guide protrusion 411 may protrude at a height C5 of 40% or more, for example, 40% to 60% of the height C4 of the receiving region 401. The height C5 of the guide protrusion 411 may be in a range of 3 mm or more, for example, 3 mm to 4 mm. The guide protrusion 411 may be spaced apart from the upper surface 41 of the second cover 410 by a predetermined distance C6. When the height C5 of the guide protrusion 411 is too high, there is a problem that the flow of the molding member 481 described below is excessively restricted. When the height C5 is too low, the molding member 481, there is a problem that the screw 416 may overflow. The guide protrusion 411 may limit the height of the molding member 481 to be filled in the cable hole 415. The guide protrusion 411 may control the height or the thickness of the molding member 481 disposed in the cable hole 415.

As shown in FIG. 15, a plurality of connection holes 417 are disposed at the bottom of the receiving region 401 of the second cover 410 and the plurality of connection holes 417 may be disposed on opposite sides or spaced apart from each other by a predetermined distance based on the signal cable 253. When one of the connection holes 417 is used as the injection port 417A and the other is used as the discharge port 417B, the injection efficiency of the molding liquid may be improved as the positions of the injection port 417A and the discharge port 417B are farther away. That is, positions of the injection port 417A and the discharge port 417B may be maximally spaced so that the molding liquid may be filled in the entire region of the receiving region 401. Since the connection hole 417 is disposed on the bottom of the second cover 410, a hole size may be enlarged and injection of molding liquid and discharge of air according to the hole size may be prevented. A diameter of the connection hole 417 may be in a range of 2 mm or more, for example, 2 mm to 3 mm.

In a process of forming the molding member 481, as shown in FIG. 15, when the liquid molding fluid is injected through the injection port 417A of the connection hole 417 disposed at the bottom of the second cover 410, the mold liquid is filled in the region between the circuit board 201 and the bottom of the second cover 410 as shown in FIG. 16. At this time, the molding liquid is injected through the injection port 471A of the connection hole 417 disposed at the bottom of the second cover 410 and an air in the receiving region 401 is discharged through the discharge port 417B, and a generation of bubble inside may be prevented. The molding liquid may be filled in the inner region A2 around the connector 251 while being filled with a predetermined height from the outer region A1 connected to the connection holes 417 (417A and 417B). When the molding liquid is cured, the molding member 481 is formed. A height of the molding member 481 filled in the connector 251 may be filled up to a height lower than the height of the connection holes 417 (417A and 417B). That is, the guide protrusion 411 may prevent the material of the molding member 481 injected through the connection hole 417 from being filled higher through the cable hole 415. For example, as shown in FIG. 16, the molding member 481 may be disposed under the locking protrusion 418 of the cable hole 415 by the guide protrusion 411, or may be formed so as not to be higher than the region between the guide protrusions 411. The molding member 481 may be disposed in an inner region and an outer region of the guide protrusion 411. It is possible to prevent a part of the molding member 481 from protruding above a horizontal straight line to the bottom 45 of the receiving region 401 and to prevent the cable gasket 240 from overflowing to and around the cable gasket 240.

The molding member 481 seals the side surface of the circuit board 201, the upper surface and the outer surface of the second recess 323 to prevent moisture and water from penetrating. The molding member 481 is in contact with the sub gasket 252 coupled to the connector 251 to seal and waterproof the connector 251 and the molding member 481, and may be prevented from an influence of the outside when the gasket 240 is separated from the cable gasket 240 and coupled with the reservoir water tank at a fastening portion of the cable gasket 240.

Figure 17:
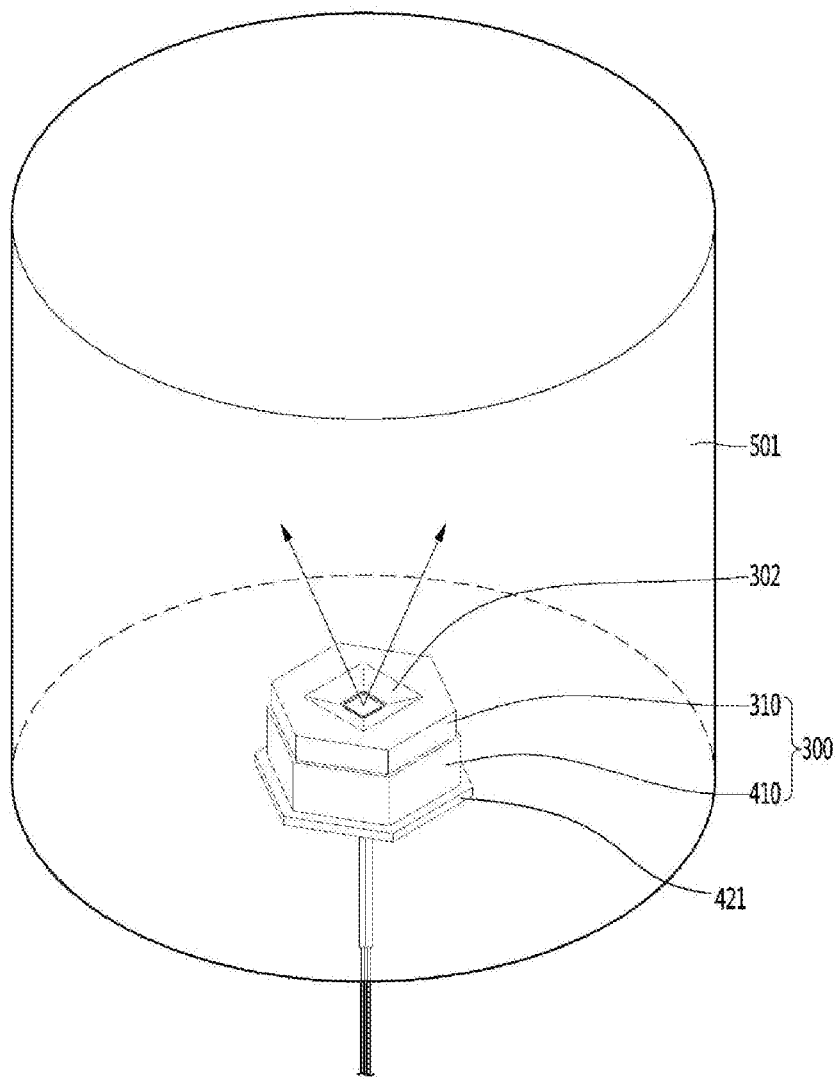
FIG. 17 is a perspective view illustrating a reservoir water tank to which a light source unit according to an embodiment of the present invention is applied.

FIG. 17 is a view illustrating an example in which a light source unit 300 according to an embodiment of the present invention is coupled to a reservoir water tank 501.

As shown in FIG. 17, the light source unit 300 may be coupled through a lower portion of the reservoir water tank 501, or may be coupled through a side surface of the reservoir water tank 501. The reservoir water tank 501 may be a water purifier or a tank of an air washer. The lower part of the light source unit 300 is caught by a stop protrusion 421 of the second cover 410 or, a bottom of the stop protrusion 421 is brought into close contact with the surface of the reservoir water tank 501, and a coupling member such as a nut of the reservoir water tank 501 is coupled to an internal screw of the connector guide portion 423 in FIG. 16. When the light source unit 300 is coupled to the reservoir water tank 501, as shown in FIG. 18, a moisture or water penetrating through an upper path F1 of the light source unit 300 is blocked by the first waterproof members 260 and 275 and the waterproof film 271 and the moisture or water penetrating through a side path F2 may be blocked by the first and second bonding portions 71 and 72 as the second waterproof member. The light source unit 300 may prevent the waterproof member from being exposed to the outside, thereby maximizing the waterproof effect without spoiling a beauty. In addition, as shown in FIG. 16, by limiting the height of the molding member 481, it is possible to reduce the problem of fastening when fastened to the reservoir water tank 501.

Figure 22:
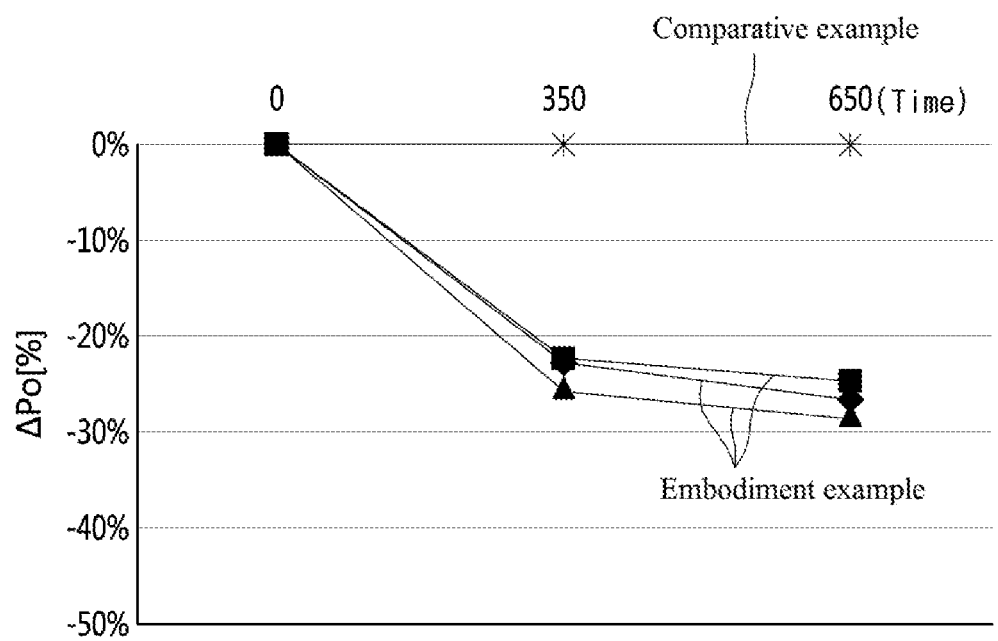
FIG. 22 is a graph comparing an example of light output of a light source unit according to a refrigeration temperature in a reservoir water tank according to an embodiment of the invention and a comparative example.
Figure 23:
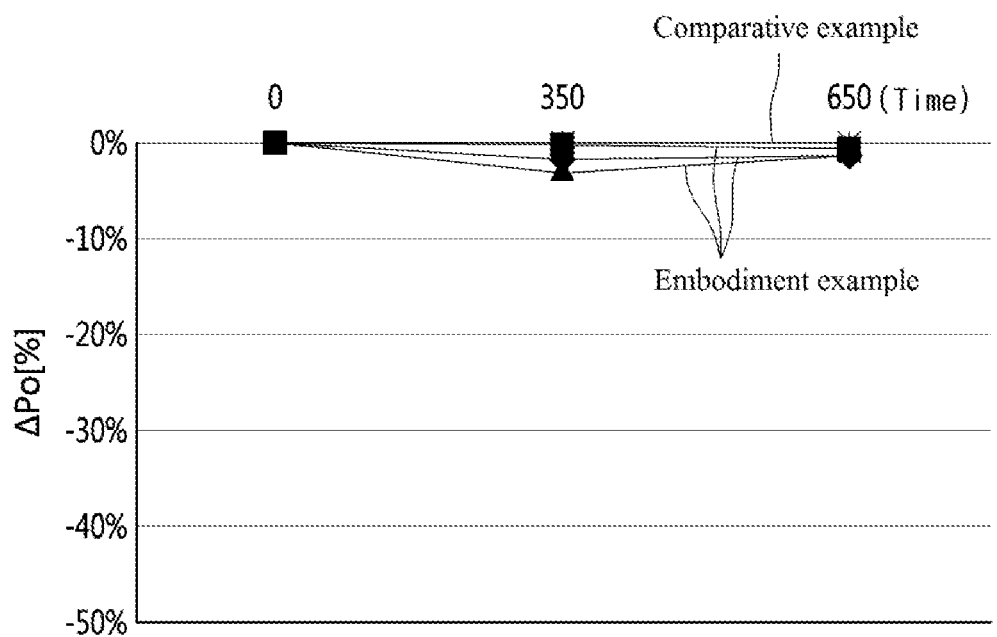
FIG. 23 is a graph comparing an example of light output of a light source unit according to a high temperature in a reservoir water tank according to an embodiment of the invention and a comparative example.

FIGS. 22 and 23 are diagrams comparing light intensities in water of light source units according to comparative example and an embodiment example of the inventive. The comparative example is a structure measuring luminous intensity under conditions not in water, and the embodiment example of the inventive is an example of measuring luminous intensity in water.

FIG. 22 shows a result of measuring the luminous intensity Po at a temperature of a general reservoir water tank, for example, 5 degrees of refrigeration, and it may be reduced by 20% to 30% as time passes. FIG. 23 shows a result of measuring at a high water temperature, and it may be seen that as the time passes, the luminous intensity Po is almost the same as the luminous intensity outside the water. Also, it was checked whether condensation of internal water vapor inside the module was confirmed, and it was found that there was no condensation.

Figure 19:
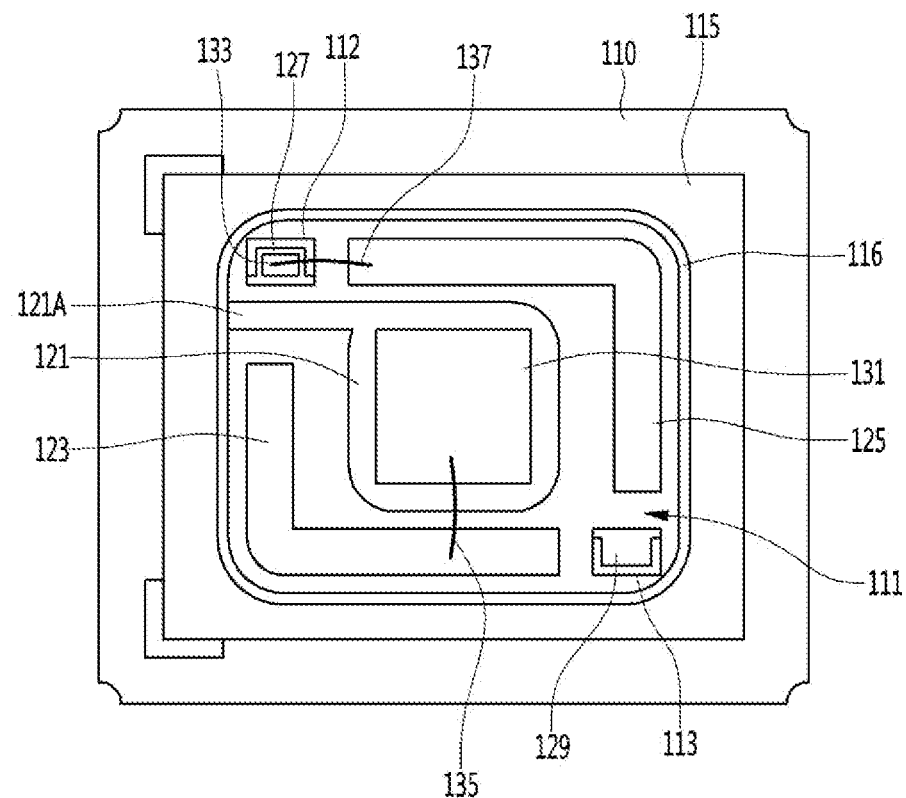
FIG. 19 is a plan view illustrating a light emitting device of a light source module according to an embodiment of the present invention.
Figure 20:
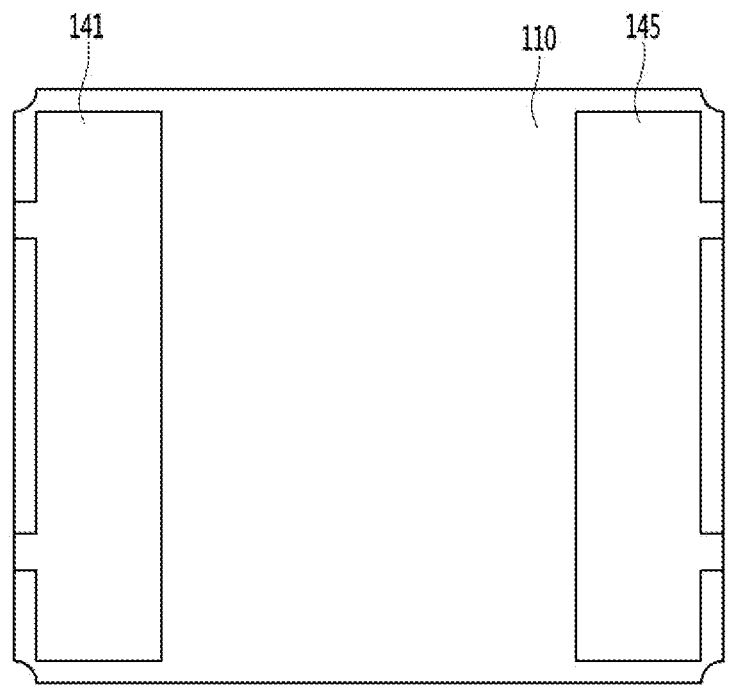
FIG. 20 is a bottom view of the light emitting device of FIG. 19.
Figure 21:
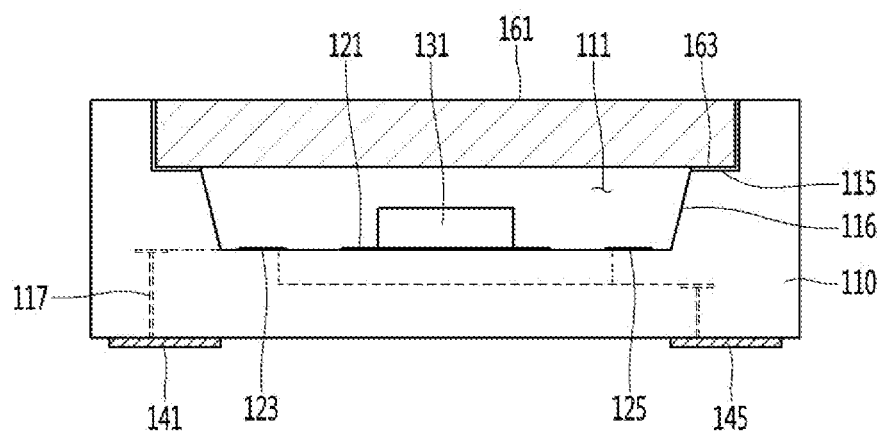
FIG. 21 is a side sectional view showing a light emitting device of the light source module of FIG. 19.

FIGS. 19 to 21 show an example of a light emitting device of a light source unit according to an embodiment of the present invention.

Referring to FIGS. 19 to 21, the light emitting device 100 includes a body 110 which has a recess 111; a plurality of electrodes 121, 123, and 125 disposed in the recess 111; a light-emitting chip 131 disposed on at least one of the plurality of electrodes 121, 123, 125; and a transparent window 161 disposed on the recess 111.

The light emitting chip 131 may include an optional peak wavelength within a wavelength range of ultraviolet to visible light. For example, the light emitting chip 131 may emit UV-C wavelengths, that is, ultraviolet wavelengths ranging from 100 nm to 280 nm.

The body 110 includes an insulating material such as a ceramic material. The ceramic material includes a low temperature co-fired ceramic (LTCC) or a high temperature co-fired ceramic (HTCC) which are co-fired. The material of the body 110 may be, for example, AlN and may be made of a metal nitride having a thermal conductivity of 140 W mK or more.

As shown in FIG. 21, a connection pattern 117 may be disposed in the body 110 and the connection pattern 117 may provide an electric connection path between the recess 111 and a lower surface of the body 110.

As shown in FIGS. 19 and 21, an upper periphery of the body 110 includes a stepped structure 115. The stepped structure 115 is a region lower than the upper surface of the body 110 and is disposed on the periphery of the upper portion of the recess 111. Although the depth of the stepped structure 115 is a depth from the upper surface of the body 110 and may be deeper than the thickness of the transparent window 161, it is not limited thereto.

The recess 111 is a region where a portion of the upper region of the body 110 is opened and may be formed at a predetermined depth from the upper surface of the body 110. For example, the bottom of the recess 111 may be deeper than the stepped structure 115 of the body 110. A position of the stepped structure 115 may be disposed in consideration of the height of the first connection member 135 connected to the light emitting chip 131 disposed on the bottom of the recess 111. Here, a direction in which the recess 111 is opened may be a direction in which light generated from the light emitting chip 131 is emitted A top view shape of the recess 111 may include a polygonal shape, a circular shape, or an elliptical shape. An edge portion of the recess 111 may have a chamfered shape, for example, a curved shape. Here, the recess 111 may be located inside the stepped structure 115 of the body 110.

A width of the lower portion of the recess 111 may be the same as or may be wider than the width of the upper portion of the recess 111. In addition, a sidewall 116 of the recess 111 may be formed to be perpendicular or inclined to an extension line of the bottom surface of the recess 111.

A plurality of sub-recesses 112 and 113 may be disposed in the recess 111. The bottom surfaces of the respective sub-recesses 112 and 113 may be disposed at a lower depth than the bottom surface of the recess 111. The spacing between the plurality of sub-recesses 112 and 113 may be spaced apart from each other to be greater than the width of the light emitting chip 131. A protection device 133 may be disposed on at least one of the plurality of sub-recesses 112 and 113. The depth of the respective sub-recesses 112 and 113 may be formed to be at least equal to or deeper than the thickness of the protection device 133. The depth of the sub-recesses 112 and 113 may be formed in a depth that the upper surface of the protection device 133 does not protrude above the bottom surface of the recess 111. Since the protection device 133 is disposed on at least one of the sub-recesses 112 and 113, the protection device 133 does not protrude on the bottom surface of the recess 111, the absorption of the light which is emitted from the light emitting chip 131 into the protection device 133 may be prevented, and a decrease in a light extraction efficiency of the light emitting device 100 and distortion of light directing angle may be prevented.

The plurality of sub-recesses 112 and 113 are disposed on the opposite sides to each other with respect to the light emitting chip 131. Accordingly, heat generated from the light emitting chip 131 may be diffused uniformly in the recess 111, thereby improving the heat resistance of the light emitting device. As another example, a protection device 133 is disposed as one of the plurality of sub-recesses 112 and 113 and a dummy may be used as the other one thereof. The protection device 133 includes a Zener diode. The protection device 133 is connected in parallel to the light emitting chip 131 to electrically protect the light emitting chip 131. The first and second sub-recesses 112 and 113 may not be formed in the recess 111 and in this case, the protection device 133 may be removed or disposed at the bottom of the recess 111.

The electrodes 121, 123 and 125 may be disposed to the recess 111 and the sub-recesses 112 and 113 and the electrodes 127 and 129 may be selectively connected to the protection device 133. The electrodes 121, 123, 125, 127, and 129 selectively supply power to the light emitting chip 131 and the protection device 133. The electrodes 121, 123, 125, 127 and 129 may selectively include a metal such as Platinum (Pt), titanium (Ti), copper (Cu), nickel (Ni), gold (Au), tantalum (Ta), aluminum (Al). At least one of the electrodes 121, 123, 125, 127, and 129 may be formed as a single layer or multiple layers. In the multilayered electrode, gold (Au) material having good bonding may be disposed on the uppermost layer thereof, titanium (Ti), chromium (Cr), and tantalum (Ta) material having good adhesion to the body 110 may be disposed on the lowermost layer thereof, and platinum (Pt), nickel (Ni), copper (Cu), or the like may be disposed on the intermediate layer between the uppermost layer and the lowermost layer thereof. It is not limited to a laminated structure of such electrodes.

Specifically, the electrodes 121, 123, and 125 may include a first electrode 121 on which the light emitting chip 131 is disposed and a second electrode 123, a third electrode 125 which are spaced apart from the first electrode 121, and fourth and fifth electrodes 127 and 129 disposed in each of the sub-recesses 112 and 113. The first electrode 121 may be disposed at the center of the bottom of the recess 111 and the second electrode 123 and the third electrode 125 may be disposed at both sides of the first electrode 121. Although any one of the first electrode 121 and the second electrode 123 may be removed, it is not limited thereto. Although the light emitting chip 131 may be disposed on plurality electrodes of the first to third electrodes 121, 123, and 125, but is not limited thereto.

One of the fourth fifth electrodes 127 and 129, for example, the fourth electrode 127 may be electrically connected to the protection device 133. The second and third electrodes 123 and 125 may be supplied with power of a first polarity and the fourth and fifth electrodes 121, 127, and 129 may be supplied with power of a second polarity. The polarity of each of the electrodes 121, 123, 125, 127, and 129 may vary depending on the electrode pattern or the connection type with each device, but is not limited thereto.

Here, if the first electrode 121 is not electrically connected to the light emitting chip 131, it may be used as a non-polar metal layer or a heat dissipation plate. Each of the electrodes 121, 123, 125, 127, and 129 may be defined as a metal layer, but is not limited thereto.

A portion 121A of the first electrode 121 extends into the body 110 and may be electrically connected to another electrode through the connection pattern 117. The first to fifth electrodes 121, 123, 125, 127, and 129 may be selectively connected to the connection pattern 117 in the body 110. For example, the connection pattern 117 connects the first electrode 121, the fourth and fifth electrodes 127 and 129 and the first pad 141, and connects the second and third electrodes 123 and 125 and the pads 145 from each other, but the present invention is not limited thereto.

As shown in FIG. 20, a plurality of pads 141 and 145 are disposed on the lower surface of the body 110. The plurality of pads 141 and 145 may include a first pad 141 and a second pad 145. The first and second pads 141 and 145 may be spaced apart from each other on the lower surface of the body 110. At least one of the first and second pads 141 and 145 may be disposed in a plurality to disperse the current path, but the present invention is not limited thereto.

A heat dissipating member (not shown) may be disposed in the body 110. The heat dissipating member may be disposed below the light emitting chip 131, that is, below the first electrode 121 to dissipate heat generated from the light emitting chip 131. The material of the heat dissipating member may be a metal, for example, an alloy.

The light emitting chip 131 may be disposed in the recess 111. The light emitting chip 131 may be an ultraviolet light emitting diode, and may be an ultraviolet light emitting diode having a wavelength ranging from 100 nm to 280 nm. That is, it is possible to emit short-wavelength ultraviolet rays of 280 nm or less. The ultraviolet wavelength has an effect of reducing various biological contaminants such as bacteria, bacteria, viruses and the like.

The light emitting chip 131 is bonded to the first electrode 121 by a conductive adhesive and may be connected to the second electrode 123 by a first connection member 135. The light emitting chip 131 may be electrically connected to the first electrode 121 and the second electrode 123 or the third electrode 125. The connection method of the light emitting chip 131 may be connected by selectively using wire bonding, die bonding, and flip bonding methods and such a bonding method may be changed depending on the chip type and the electrode position of the chip. The protection device 133 is bonded to the fourth electrode 127 and may be connected to the third electrode 125 by a second connection member 137 and may be electrically connected to the third electrode 125 and the fourth electrode 127. The first and second connection members 135 and 137 include, for example, a wire. The protection device 133 may be removed and disposed on the circuit board 201 in FIG. 1.

The light emitting chip 131 may be formed of a compound semiconductor of Group II and VI elements, or a compound semiconductor of Group III and V elements. The light emitting device may selectively include a semiconductor light emitting device manufactured using compound semiconductors such as AlInGaN, InGaN, AlGaN, GaN, GaAs, InGaP, AlInGaP, InP and InGaAs-based compound semiconductor. The light emitting chip 131 may include an n-type semiconductor layer, a p-type semiconductor layer, and an active layer and may be implemented in pairs such as an InGaN/GaN, InGaN/AlGaN, InGaN/InGaN, GaN/AlGaN, AlGaN/AlGaN, InAlGaN/InAlGaN, AlGaAs/GaAs, InGaAs/GaAs, InGaP/GaP, AlInGaP/InGaP, and InP/GaAs.

As shown in FIG. 21, the transparent window 161 is disposed on the recess 111. The transparent window 161 includes a glass material such as quartz glass. Accordingly, the transparent window 161 may be defined as a material capable of transmitting light emitted from the light emitting chip 131, for example, without damage such as intermolecular bond breakdown due to ultraviolet wavelength.

An outer periphery of the transparent window 161 is coupled to the stepped structure 115 of the body 110. An adhesive layer 163 is disposed between the transparent window 161 and the step structure 115 of the body 110 and the adhesive layer 163 includes a resin material such as silicone or epoxy. The transparent window 161 may be formed to have a width wider than the bottom width of the recess 111. The bottom surface area of the transparent window 161 may be larger than the bottom surface area of the recess 111. Accordingly, the transparent window 161 may be easily coupled to the step structure 115 of the body 110.

The transparent window 161 may be spaced apart from the light emitting chip 131. It is possible to prevent the transparent window 161 from being expanded due to the heat generated by the light emitting chip 131 by being separated from the light emitting chip 131. The space under the transparent window 161 may be an empty space, or may be filled with a non-metallic or metallic chemical element, but the present invention is not limited thereto. A lens may be coupled onto the transparent window 161, but the present invention is not limited thereto. Further, a molding member may be further disposed on the side surface of the body 110 to perform moisture and device protection.

The light emitting device and the light source unit having the light emitting device according to the embodiments of the present invention may be used as an apparatus for sterilizing an indoor unit, an evaporator, and a condensate of a refrigerator, and a sterilizing device in an appliance such as an air washer, a reservoir water tank and a discharging water sterilization device, and a sterilizing device in a toilet. Such a sterilization apparatus may optionally include the waterproof film and the waterproof members disclosed above.

The features, structures, effects and the like described in the embodiments are included in at least one embodiment of the present invention, and are not necessarily limited to only one embodiment. Further, the features, structures, effects, and the like illustrated in the embodiments may be combined and modified by other persons having ordinary skill in the art to which the embodiments belong. Therefore, it should be understood that the present invention is not limited to these combinations and modifications.

The invention claimed is:

1. A light source unit comprising:
a first cover having an open region at an upper portion and a recess in which a lower portion is opened;
a second cover coupled to the lower portion of the first cover;
a light source module disposed between the first and second covers, the light source module having a circuit board and a light emitting device on the circuit board;
a waterproof film disposed on the light emitting device and facing an upper surface of the circuit board;
a first gasket having a first opening therein and disposed between the waterproof film and the circuit board; and
a second gasket having a second opening therein and disposed on the waterproof film;
wherein the first cover includes a first outer wall around an outer periphery thereof,
the second cover includes a second outer wall around an outer periphery thereof,
wherein one of the first outer wall and the second outer wall has a protrusion and the other has a groove,
the protrusion is coupled to the groove,
wherein the light source unit includes a bonding portion disposed between the first outer wall and the second outer wall,
wherein the light emitting device is disposed in the first opening of the first gasket,
an upper surface of the light emitting device faces to the second opening of the second gasket and the open region of the first cover, and
wherein the first gasket has a thickness greater than a thickness of the light emitting device.

2. The light source unit of claim 1,
wherein the bonding portion is continuously disposed along the first outer wall of the first cover and the second outer wall of the second cover,
wherein the bonding portion comprises a plurality of bonding portions disposed a different region of the first outer wall and the second outer wall facing each other, and
wherein the plurality of bonding portions have different heights.

3. The light source unit of claim 2,
wherein the first gasket includes a plurality of upper protrusions on an upper surface thereof, a first concave region between the plurality of upper protrusions, a plurality of lower protrusions on a lower surface thereof, and a second concave region between the plurality of lower protrusions,
wherein the plurality of upper protrusions and the plurality of lower protrusions are disposed to overlap in a vertical direction.

4. The light source unit of claim 1,
wherein the first cover includes a first recess in which the first and second gaskets and the waterproof film are disposed; and a second recess in which the circuit board is disposed, and a fastening portion for fastening the circuit board to the first cover with a fastening member outside the first recess.

5. The light source unit of claim 4,
wherein the circuit board includes a plurality of fastening holes to which the fastening member are fastened, and a metal layer disposed along an outer periphery of the circuit board.

6. The light source unit of claim 1,
wherein the first opening has a width greater than a width of the second opening in a first direction,
wherein the second opening has the width smaller than the width of the first opening in the first direction and has the width greater than a width of the light emitting device,
wherein the width of the second opening in the first direction is greater than the width of the open region.

7. The light source unit of claim 1,
wherein the protrusion is protruded in a direction from a lower surface of the first outer wall of the first cover toward the second cover,
the groove is recessed on the second outer wall of the second cover,
the bonding portion comprises a first bonding portion bonded to at least one of a surfaces of the protrusion and the groove; and a second bonding portion bonded to an inside of the lower surface of the first outer wall and an inside of the upper surface of the second outer wall,
the first and second bonding portions are formed of at least one of a materials of the first and second covers,
the first bonding portion is lower than a height of the second bonding portion,
the first bonding portion is disposed on an outer side of the second bonding portion,
the first and second bonding portions are merged to the first and second covers.

8. The light source unit of claim 1,
the light emitting device emits a wavelength band of 100 nm to 280 nm,
wherein the waterproof film, the first and second gaskets comprise a fluororesin material.

9. The light source unit of claim 1, comprising:
a guide protrusion protruding toward the first cover from a receiving region of the second cover and a connector coupled to the circuit board on an inner side of the guide protrusion,
wherein the first cover includes a concave portion having the open region to the upper portion thereof,
wherein the recess includes an inclined side surface,
wherein at least a part of the light emitting device or at least a part of the waterproof film protrudes into the open region.

10. The light source unit of claim 1, comprising:
a molding member disposed in the recess of the first cover and a receiving region of the second cover,
wherein the second cover includes a cable hole connection to the receiving region therein and a guide protrusion protruding in an upward direction of the second cover along an periphery of the cable hole,
wherein the molding member is disposed in an inner region and an outer region of the guide protrusion, and
wherein the second cover includes a connecting hole disposed on opposite sides of each other around the cable hole on a bottom of the receiving region.

11. A light source unit comprising:
a first cover having an open region at an upper portion and a recess in which a lower portion is opened;
a second cover coupled to the lower portion of the first cover;
a light source module disposed between the first and second covers, the light source module having a circuit board and a light emitting device on the circuit board;
a waterproof film disposed on the light emitting device and facing an upper surface of the circuit board;
a first gasket having a first opening therein and disposed between the waterproof film and the circuit board;
a second gasket having a second opening therein and disposed on the waterproof film; and
a molding member disposed in the recess of the first cover and a receiving region of the second cover,
wherein the first cover includes a first outer wall around an outer periphery thereof,
the second cover includes a second outer wall around an outer periphery thereof,
wherein light emitting device is disposed in the first opening of the first gasket,
wherein an upper surface of the light emitting device faces to the second opening of the second gasket and the open region of the first cover.

12. The light source unit of claim 11, wherein one of the first outer wall and the second outer wall has a protrusion and the other has a groove,
wherein the protrusion is coupled to the groove,
wherein the light source unit includes a bonding portion disposed between the first outer wall and the second outer wall.

13. The light source unit of claim 12, wherein the bonding portion is continuously disposed along the first outer wall of the first cover and the second outer wall of the second cover,
wherein the bonding portion is continuously disposed along the first outer wall of the first cover and the second outer wall of the second cover,
wherein the bonding portion comprises a plurality of bonding portions disposed a different region of the first outer wall and the second outer wall facing each other, and
wherein the plurality of bonding portions have different heights.

14. The light source unit of claim 12, wherein the first gasket has a thickness greater than a thickness of the light emitting device,
wherein the first gasket includes a plurality of upper protrusions on an upper surface thereof, a first concave region between the plurality of upper protrusions, a plurality of lower protrusions on a lower surface thereof, and a second concave region between the plurality of lower protrusions,
wherein the plurality of upper protrusions and the plurality of lower protrusions are disposed to overlap in a vertical direction.

15. The light source unit of claim 12, wherein the first cover includes a first recess in which the first and second gaskets and the waterproof film are disposed; and a second recess in which the circuit board is disposed, and
a fastening portion for fastening the circuit board to the first cover with a fastening member outside the first recess.

16. The light source unit of claim 15, wherein the light emitting device emits a wavelength band of 100 nm to 280 nm,
wherein the waterproof film, the first and second gaskets comprise a fluororesin material, and
wherein the circuit board includes a plurality of fastening holes to which the fastening member are fastened; and a metal layer disposed along an outer periphery of the circuit board.

17. The light source unit of claim 12, wherein the protrusion is protruded in a direction from a lower surface of the first outer wall of the first cover toward the second cover,
wherein the groove is recessed on the second outer wall of the second cover,
wherein the bonding portion comprises a first bonding portion bonded to at least one of a surfaces of the protrusion and the groove; and a second bonding portion bonded to an inside of the lower surface of the first outer wall and an inside of the upper surface of the second outer wall,
wherein the first and second bonding portions are formed of at least one of a materials of the first and second covers,
wherein the first bonding portion is lower than a height of the second bonding portion,
wherein the first bonding portion is disposed on an outer side of the second bonding portion, and
the first and second bonding portions are merged to the first and second covers.

18. The light source unit of claim 11, wherein the second cover includes a cable hole connected to the receiving region therein and a guide protrusion protruding in an upward direction of the second cover along a circumference of the cable hole, and
wherein the molding member is disposed in an inner region and an outer region of the guide protrusion.

19. The light source unit of claim 11, wherein the first opening has a width greater than a width of the second opening in a first direction,
wherein the second opening has the width smaller than the width of the first opening in the first direction and has the width greater than a width of the light emitting device,
wherein the width of the second opening in the first direction is greater than the B width of the open region.

20. The light source unit of claim 11, comprising:
a guide protrusion protruding toward the first cover from the receiving region of the second cover and a connector coupled to the circuit board on an inner side of the guide protrusion,
wherein the first cover includes a concave portion having the open region to the upper portion thereof,
wherein the recess includes an inclined side surface,
wherein at least a part of the light emitting device or at least a part of the waterproof film protrudes into the open region.

* * * * *